US010865378B2

(12) United States Patent
Desai et al.

(10) Patent No.: US 10,865,378 B2
(45) Date of Patent: Dec. 15, 2020

(54) THIN FILM CELL ENCAPSULATION DEVICES

(71) Applicant: The Regents of the University of California, Oakland, CA (US)

(72) Inventors: Tejal A. Desai, San Francisco, CA (US); Crystal Nyitray, San Francisco, CA (US); Ryan Chang, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/111,773

(22) Filed: Aug. 24, 2018

(65) Prior Publication Data
US 2019/0093069 A1     Mar. 28, 2019

Related U.S. Application Data

(63) Continuation of application No. 15/713,098, filed on Sep. 22, 2017, now Pat. No. 10,087,413, which is a
(Continued)

(51) Int. Cl.
*A61K 35/39*     (2015.01)
*C12N 5/00*     (2006.01)
(Continued)

(52) U.S. Cl.
CPC .......... *C12N 5/0012* (2013.01); *A61K 9/0024* (2013.01); *A61K 47/34* (2013.01); *C08G 63/08* (2013.01); *C12N 5/0676* (2013.01)

(58) Field of Classification Search
CPC .................................................... A61K 35/39
See application file for complete search history.

(56) References Cited

U.S. PATENT DOCUMENTS 9,005,960 B2    4/2015   Legeay et al.
D747,467 S      1/2016   Green
(Continued)

FOREIGN PATENT DOCUMENTS

CN     102282254     12/2011
WO      9639098      12/1996
(Continued)

OTHER PUBLICATIONS

Avid Nano, Advancing Dynamic Light Scattering, https://hamptonresearch.com/uploads/docurnents/ramc/RAMC2011_Commercial%20Presentation%20Avid%20Nano.pdf, 2011.*
(Continued)

*Primary Examiner* — Rosanne Kosson
(74) *Attorney, Agent, or Firm* — Edward J. Baba; Bozicevic, Field & Francis LLP

(57) ABSTRACT

Thin film devices, e.g., multilayer thin film devices, that encapsulate cells for transplantation into a subject are provided. Also provided are methods of using and methods of preparing the subject devices. The thin film devices include a first porous polymer layer and a second porous polymer layer that define a lumen therebetween and encapsulate a population of cells within the lumen. The thin film devices can promote vascularization into the lumen of the device via the pores in the first polymer layer and/or second polymer layer; limit foreign body response to the device; limit ingress of cells, immunoglobulins, and cytokines into the lumen via the first and the second polymer layers; and release from the first polymer layer and/or the second polymer layer molecules secreted by the population of cells.

20 Claims, 11 Drawing Sheets

Related U.S. Application Data continuation of application No. PCT/US2016/023808, filed on Mar. 23, 2016.

(60) Provisional application No. 62/136,997, filed on Mar. 23, 2015.

(51) Int. Cl.

| | |
|---|---|
| A61K 9/00 | (2006.01) |
| A61K 47/34 | (2017.01) |
| C08G 63/08 | (2006.01) |
| C12N 5/071 | (2010.01) |

(56) References Cited

U.S. PATENT DOCUMENTS

| | | |
|---|---|---|
| D747,468 S | 1/2016 | Green |
| D747,798 S | 1/2016 | Green |
| D750,769 S | 3/2016 | Green |
| D750,770 S | 3/2016 | Green |
| D755,986 S | 5/2016 | Green et al. |
| D760,399 S | 6/2016 | So et al. |
| D761,423 S | 7/2016 | So et al. |
| D761,424 S | 7/2016 | So et al. |
| 9,433,557 B2 | 9/2016 | Green et al. |
| 9,526,880 B2 | 12/2016 | So et al. |
| 10,087,413 B2 | 10/2018 | Desai et al. |
| 2008/0292690 A1 | 11/2008 | Wang |
| 2010/0124564 A1 | 5/2010 | Martinson et al. |
| 2010/0196439 A1 | 8/2010 | Beck et al. |
| 2011/0300191 A1 | 12/2011 | Barkai et al. |
| 2014/0170204 A1 | 6/2014 | Desai et al. |
| 2014/0257515 A1 | 9/2014 | So et al. |
| 2014/0271843 A1 | 9/2014 | Ma et al. |
| 2016/0310541 A1 | 10/2016 | Bou Aoun et al. |

FOREIGN PATENT DOCUMENTS

| | | |
|---|---|---|
| WO | WO 2011/025977 | 3/2011 |
| WO | 2014173441 A1 | 10/2014 |
| WO | WO 2016/028774 | 2/2016 |

OTHER PUBLICATIONS

Whittingham et al., "Insulin at pH 2: structural analysis of the conditions promoting insulin fibre formation," J Mol Biol 318:479-490, 2002.*

Kendrick et al., "A transient expansion of the native state precedes aggregation of recombinant human interferon-γ," Proc Natl Acad Sci USA 95:14142-14146, 1998.*

Yip et al., "Molecular weight of human gamma interferon is similar to that of other human interferons," Science 215(4531):411-413, 1982.*

Abedalwafa, et al. Biodegradable Poly-Epsilon-Caprolactone (Pcl) For Tissue Engineering Applications: A Review. Review On Advanced Materials Science 34 (2013): 123-140.

Angius, et al. A systematic review of animal models used to study nerve regeneration in tissue-engineered scaffolds. Biomaterials 33.32 (2012): 8034-8039.

Anzai, et al. Poly(£-caprolactone) (PCL)-polymeric micelle hybrid sheets for the incorporation and release of hydrophilic proteins. Colloids and Surfaces B: Biointerfaces 127 (2015): 292-299.

Atkinson, et al. Type 1 diabetes. Lancet 383.9911 (2014): 69-82.

Bastiaens, Systems Biology: When it is time to die. Nature 459 (2009): 334-335.

Bernards, et al. Nanoscale porosity in polymer films: fabrication and therapeutic applications. Soft Matter 6.8 (2010): 1621-1631.

Bernards, et al. Nanostructured Thin Film Polymer Devices for Constant-Rate Protein Delivery. Nano Letters 12.10 (2012): 5355-5361.

Bernards, et al. Nanotemplating of Biodegradable Polymer Membranes for Constant-Rate Drug Delivery. Advanced Materials 22 (2010): 2358-2362.

Bernards, et al. Ocular biocompatibility and structural integrity of micro- and nanostructured poly (caprolactone) films. Journal of Ocular Pharmacology and Therapeutics 29.2 (2013): 249-257.

Buder, et al. Encapsulated Islet Transplantation: Strategies and Clinical Trials. Immune Network 13.6 (2013): 235-239.

Calafiore, et al. Clinical application of microencapsulated islets: Actual prospectives on progress and challenges. Advanced Drug Delivery Reviews 67 (2014): 84-92.

Chang, et al. Nanoporous Immunoprotective Device for Stem Cell Derived # Cell Replacement Therapy. ACS Nano, Just Accepted Manuscript • DOI: 10.1021/acsnano.7b01239 • Publication Date (Web): Aug 1, 2017. Downloaded from http://pubs.acs.org on Aug. 2, 2017.

Cornolti, et al. Effect of Micro- and Macroencapsulation on Oxygen Consumption by Pancreatic Islets. Cell Transplantation 18 (2009): 195-201.

Faveri, et al. Bio-inspired hybrid microelectrodes: a hybrid solution to improve long-term performance of chronic intracortical implants. Frontiers in Neuroengineering 7 (2014): 1-12.

Fonseca, et al. *Echinacea purpurea* (L.) Moench modulates human T-cell cytokine response. International Immunopharmacology 19.1 (2013): 94-102.

Fowler, et al. Assessment of Pancreatic Islet Mass after Islet Transplantation Using In Vivo Bioluminescence Imaging. Transplantation 79.7 (2005): 768-776.

Hatziavramidis, et al. Pancreatic Islet Cell Transplantation: An Update. Annals of Biomedical Engineering 41.3 (2013): 469-476.

Huang, et al. Peptide Hydrogelation and Cell Encapsulation for 3D Culture of MCF-7 Breast Cancer Cells. Plos One 8.3 (2013): e59482-e59482.

International Search Report for PCT/US2016/023808 dated Jun. 27, 2016.

Kim, et al. Controlled growth of inorganic nanorod arrays using graphene nanodot seed layers. Nanotechnology 25 (2014): 135609 (6pp).

Lathuiliere, et al. A high-capacity cell macroencapsulation system supporting the long-term survival of genetically engineered allogeneic cells. Biomaterials 35 (2014): 779-791.

Ledeuil, et al. New insights into micro/nanoscale combined probes (nanoAuger, µXPS) to characterize Ag/Au@SiO2 core-shell assemblies. Nanoscale 6 (2014): 11130-11140.

Lei, et al. Zero-order release of 5-fluorouracil from PCL-based films featuring trilayered structures for stent application. European Journal of Pharmaceutics and Biopharmaceutics 78 (2011): 49-57.

Libert, A nervous connection. Nature 421 (2003): 328-329.

Lin, et al. Design of a microporous controlled delivery system for theophylline tablets. Journal of Controlled Release 89 (2003): 179-187.

Lu, et al. Effects of amphiphilic PCL-PEG-PCL copolymer addition on 5-fluorouracil release from biodegradable PCL films for stent application. International Journal of Pharmaceutics 419 (2011): 77-84.

Ludwig, et al. Transplantation of human islets without immunosuppression. Proceedings of the National Academy of Sciences 110.47 (2013): 19054-19058.

Martin, et al. Bioreactors for tissue mass culture: Design, characterization, and recent advances. Biomaterials 26 (2005): 7481-7503.

Mendelsohn, et al. Patterning of Mono- and Multi-layered Pancreatic β-cell Clusters. Langmuir 26.12 (2010): 9943-9949.

Miyazaki, et al. Establishment of a Pancreatic β Cell Line That Retains Glucose-Inducible Insulin Secretion: Special Reference to Expression of Glucose Transporter Isoforms. Endocrinology 127.1 (1990): 126-132.

Nyitray et al. (2015) "Polycaprolactone thin-film micro- and nanoporous cell-encapsulation devices" ACS nano 9(6):5675-5682.

Orlando, et al. Cell Replacement Strategies Aimed at Reconstitution of the β-Cell Compartment in Type 1 Diabetes. Diabetes 63 (2014): 1433-1444.

Rentsch, et al. Embroidered and surface coated polycaprolactone-co-lactide scaffolds; A potential graft for bone tissue engineering. Biomatter 2.3 (2012): 158-165.

(56) References Cited

OTHER PUBLICATIONS

Robles, et al. Current Status of Islet Encapsulation. Cell Transplantation 23 (2014): 1321-1348.
Roff, et al. The significance of interferon-g in HIV-1 pathogenesis, therapy, and prophylaxis. Frontier in Immunology 4 (2014): 1-11.
Rong, et al. PCL films incorporated with paclitaxel/5-fluorouracil: Effects of formulation and spacial architecture on drug release. International Journal of Pharmaceutics 427 (2012): 242-251.
Scharp, et al. Encapsulated islets for diabetes therapy: History, current progress, and critical issues requiring solution. Advanced Drug Delivery Reviews 67 (2014): 35-73.
Schweicher, et al. Membranes to achieve immunoprotection of transplanted islets. Frontiers in Bioscience 19 (2014): 49-76.
Shah, Encapsulated stem cells for cancer therapy. Biomatter 3.1 (2013): 1-7.
Shapiro, et al. Islet transplantation in seven patients with type 1 diabetes Mellitus using a glucocorticoid-free immunosuppressive regimen. The New England Journal Of Medicine 343.4 (2000): 230-238.
Skelin, et al. Pancreatic beta cell lines and their applications in diabetes mellitus research. ALTEX 27 (2010): 105-113.
Song, et al. In vitro culture and oxygen consumption of NSCs in size-controlled neurospheres of Ca-alginate/gelatin microbead. Materials Science and Engineering C 40 (2014): 197-203.
Steedman, et al. Enhanced differentiation of retinal progenitor cells using microfabricated topographical cues. Biomed Microdevices 12 (2010): 363-369.
Szot, et al. Video Article: Murine Pancreatic Islet Isolation. Journal of Visualized Experiments (2007): 1-2.
Tomei, et al. Device design and materials optimization of conformal coating for islets of Langerhans. Proceedings of the National Academy of Sciences 111.29 (2014): 10514-10519.
Tracey, et al. The inflammatory reflex. Nature 20 (2002): 853-859.
Wang, et al. TNF-α Induces Two Distinct Caspase-8 Activation Pathways. Cell 133 (2003): 693-703.
Ward, A Review of the Foreign-body Response to Subcutaneously-implanted Devices: The Role of Macrophages and Cytokines in Biofouling and Fibrosis. Journal of Diabetes Science and Technology 2.5 (2008): 768-777.
Ward, et al. The effect of microgeometry, implant thickness and polyurethane chemistry on the foreign body response to subcutaneous implants. Biomaterials 23 (2002): 4185-4192.
Weir, Islet encapsulation: advances and obstacles. Diabetologia 56 (2013): 1458-1461.
Wendt, et al. Potential and Bottlenecks of Bioreactors in 3D Cell Culture and Tissue Manufacturing. Advanced Materials 21 (2009): 3352-3367.
Yang, et al. Multiparameter Screening Reveals a Role for Na+ Channels in Cytokine-Induced B-Cell Death. Original Research 28.3 (2014): 406-417.
Zhang, et al. Near-Room-Temperature Production of Diameter-Tunable ZnO Nanorod Arrays through Natural Oxidation of Zinc Metal. Chemistry—A European Journal 11 (2005): 3149-3154.
U.S. Appl. No. 15/713,098 Notice of Allowance dated Jun. 25, 2018.
U.S. Appl. No. 15/713,098 Notice of Allowance dated Jun. 29, 2018.
U.S. Appl. No. 15/713,098 Notice of Allowance dated May 23, 2018.
U.S. Appl. No. 15/713,098 Office Action dated Mar. 1, 2018.

\* cited by examiner

THIN FILM CELL ENCAPSULATION DEVICES

CROSS-REFERENCE TO RELATED APPLICATIONS

This application is a continuation application of U.S. patent application Ser. No. 15/713,098, filed Sep. 22, 2017, now U.S. Pat. No. 10,087,413, which is a continuation application of International Patent Application No. PCT/US2016/023808, filed Mar. 23, 2016, which claims the benefit of U.S. Provisional Application No. 62/136,997, filed Mar. 23, 2015, which applications are herein incorporated by reference in their entirety.

INTRODUCTION

Cell replacement therapy has seen unprecedented progress in the past few years, including the ability to achieve insulin independence in humans through islet transplantation (Atkinson et al., Lancet 2014, 383, 69-82; Orlando et al., Diabetes 2014, 63, 1433-1444; Hatziavramidis et al., Ann. Biomed. Eng. 2013, 41, 469-476). Advancements in stem cell technology hold potential to overcome donor shortages for many patients, who can benefit from islet replacement therapy. In particular, stem-cell-derived beta cells offer a promising new cell source for achieving insulin independence. Unfortunately, life-long systemic immunosuppression is required to protect transplanted cells from being rejected putting patients at risk of organ damage, infection and malignancies (Ludwig et al., Proc. Natl. Acad. Sci. U.S.A 2013, 110, 19054-19058; Shapiro et al., N. Engl. J. Med. 2000, 343, 230-238). Cell encapsulation provides an alternative approach to protect transplanted cells without the complications associated with immunosuppression. While a number of strategies are being investigated (Huang et al., PLoS One 2013, 8; Shah, Biomatter 2013, 3, 1-7; Song et al., Mater. Sci. Eng. C. Mater. Biol. Appl. 2014, 40, 197-203; De Faveri et al., Neuroeng. 2014, 7, 7; Robles et al., Cell Transplant. 2013; Tomei et al., Proc. Natl. Acad. Sci. U.S.A 2014, 111, 10514-10519), there are several challenges associated with these approaches: retrievability, control over pore dimensions, biocompatibility, scalability, and reproducible fabrication methods.

The key function of an encapsulation device is to create an environment that allows for normal insulin secretion in response to fluctuating blood glucose, while maintaining cell viability through sequestration from the immune system and effective nutrient and waste exchange. With the goal of creating immune-protected beta cells, a variety of micro- and macro-encapsulating approaches have been developed over the past several decades (Scharp et al., Adv. Drug Deliv. Rev. 2014, 67-68, 35-73; Weir, Diabetologia 2013, 56, 1458-1461; Buder et al., Immune Netw. 2013, 13, 235-239, Julien et al., Fontiers Biosci. (Landmark Ed.) 2014, 19, 49-76). The fundamental distinction between micro- and macro-devices is a matter of scale: micro-encapsulation approaches encapsulate a single cell or islet, which maximizes surface area to volume ratios and promotes improved nutrient exchange (Cala et al., Clinical Application of Microencapsulated Islets: Actual Prospectives on Progress and Challenges. 2014, 68, 84-92; Cornolti et al., Cell 2009, 18, 195-201). However, there is limited control of membrane thickness and pore size with micro-encapsulation.

Additionally, since islets are individually encapsulated, thousands of microdevices are required for each transplant, and capsule size makes live imaging and tracking a significant challenge. Conversely, macro-encapsulation devices house many cells or islets (Lathuilière et al., Biomaterials 2014, 35, 779-791). These larger devices allow for greater control over membrane parameters, such as pore size and porosity, but are plagued by limited nutrient diffusion and cell response due to the device thickness and large device reservoir. In addition to these challenges, the sharp rigid structures typically associated with macro-encapsulation devices can lead to a foreign body response and subsequent device failure from fibrotic encapsulation (Ward, J. Diabetes Sci. Technol. 2008, 2, 768-777; Ward et al., Biomaterials 2002, 23, 4185-4192).

The present disclosure address these as well as other needs in the field of delivery of biological material to a subject in need thereof.

SUMMARY

Thin film devices that encapsulate cells for transplantation of the cells into a subject are provided. Also provided are methods of preparing the subject devices and methods for using the subject devices. The thin film devices include a first layer, a population of cells and a second layer, where the first layer and the second layer are in contact with one another around the periphery of the cells disposed between the first layer and the second layer. The thin film medical devices are used in methods for providing encapsulated transplanted cells in a subject. The method includes transplanting the thin film device into a subject; promoting vascularization of the device and/or; inhibiting foreign body response and/or; limiting ingress of cytokines, immunoglobulins and cells into the device; and releasing molecules secreted by the encapsulated cells.

In certain embodiments, a method for transplanting cells in a subject is disclosed. The method may include: (a) providing a thin film device comprising: (i) a first nanoporous or microporous polymer layer; (ii) a second nanoporous or microporous polymer layer, wherein the first and second layers define a lumen between the first and second layers; and (iii) a population of cells disposed in the lumen between the first and second layers, wherein first and second polymer layers are each less than 15 µm thick, and the device has a surface area of 1 $cm^2$ to 5 $cm^2$, (b) transplanting the device into a subject, wherein one or more of: (i) vascularization into the lumen of the device via the pores in the first polymer layer and/or second polymer layer; (ii) a limited foreign body response to the device; (iii) a limited ingress of cells, immunoglobulins, and cytokines into the lumen via the first and the second polymer layers, is observed.

In certain embodiments, the method may further include releasing from the first polymer layer and/or the second polymer layer molecules secreted by the population of cells.

In certain embodiments, the population of cells may survive for at least one month after the transplanting.

In certain embodiments, the population of cells comprises pancreatic islet cells and wherein the pancreatic islet cells sealed inside the device respond to glucose level of the subject by secreting insulin. In certain embodiments, the subject has or is predisposed to developing diabetes.

In certain embodiments, the first and second polymer layers are nanoporous polymer layers and may each include a supporting layer, such as, a microporous backing layer adhered to a surface of the nanoporous polymer layer.

In certain embodiments, the first and second polymer layers are microporous polymer layers.

In certain embodiments, the first polymer layer is a nanoporous polymer layer and the second polymer layer is a microporous polymer layer.

In certain embodiments, the first and second polymer layers are fabricated using the polymer poly-caprolactone (PCL).

In certain embodiments, the first and second polymer layers are sealed along the entire periphery of the device thereby providing a closed lumen.

In certain embodiments, the lumen comprises an opening at which the first and second polymer layers are not sealed to each other.

In certain embodiments, the lumen comprises an opening at which the first and second layers are not in contact with each other, the device further comprising a tubing comprising a first end and a second end distal to the first end, wherein the first end of the tubing is positioned in the opening and the second end is configured to introduce the population of cells into the lumen.

In certain embodiments, the lumen comprises a first opening and a second opening at which the first and second layers are not in contact with each other, the device further comprising a first tubing and a second tubing, each of the first and second tubing comprising a first end and a second end distal to the first end, wherein the first end of the first tubing is positioned in the first opening and the first end of the second tubing is positioned in the second opening, and wherein the second end of each tubing is used for ingress or egress of fluids from the lumen.

In certain embodiments, the method comprises after the transplanting, attaching the second ends of the first and second tubing to a fill port. In certain embodiments, the fill port comprises a first chamber in fluid communication at the fill port with the second end of the first tubing; and a second chamber in fluid communication at the fill port with the second end of the second tubing.

In certain embodiments, a thin film device for transplanting cells in a subject is provided. The device includes a first nanoporous or microporous polymer layer; a second nanoporous or microporous polymer layer, wherein the first and second polymer layers define a lumen between the first and second polymer layers; and a population of cells disposed in the lumen between the first and second polymer layers, wherein first and second layers are less than 15 µm thick, and the device has a surface area of 1 $cm^2$ to 5 $cm^2$, and wherein (a) the pores in the first and second polymer layers limit ingress of cells, immunoglobulins, and cytokines into the lumen via the first and the second layers, and/or (b) the pores are sized to promote vascularization into the lumen of the device, and/or (c) the device is configured to limit foreign body response to the transplanted device, and (d) the pores are sized to release molecules secreted by the population of cells. In certain embodiments, first and second polymer layers are nanoporous layers and may each include a supporting layer, such as, a microporous backing layer adhered to a surface of the nanoporous polymer layer.

In certain embodiments, a method for making a device disclosed herein is provided. The method may include placing a first nanoporous or microporous polymer layer over a second nanoporous or microporous polymer layer, wherein the first and second polymer layers are similarly dimensioned; sealing the first and the second polymer layers along the periphery of the polymer layers leaving an unsealed area at a location along the periphery to provide an opening for access to a lumen defined between the first and second layers and the periphery of the polymer layers at which the polymer layers are sealed together, placing a population of cells into the lumen through the opening; and sealing the opening. In certain embodiments, the first and second polymer layers are sealed together via application of heat. In certain embodiments, the first and second polymer layers are sealed together via application of an adhesive.

These and other objects, advantages, and features of the invention will become apparent to those persons skilled in the art upon reading the details of the devices and methods as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DEFINITIONS

Figure 1:
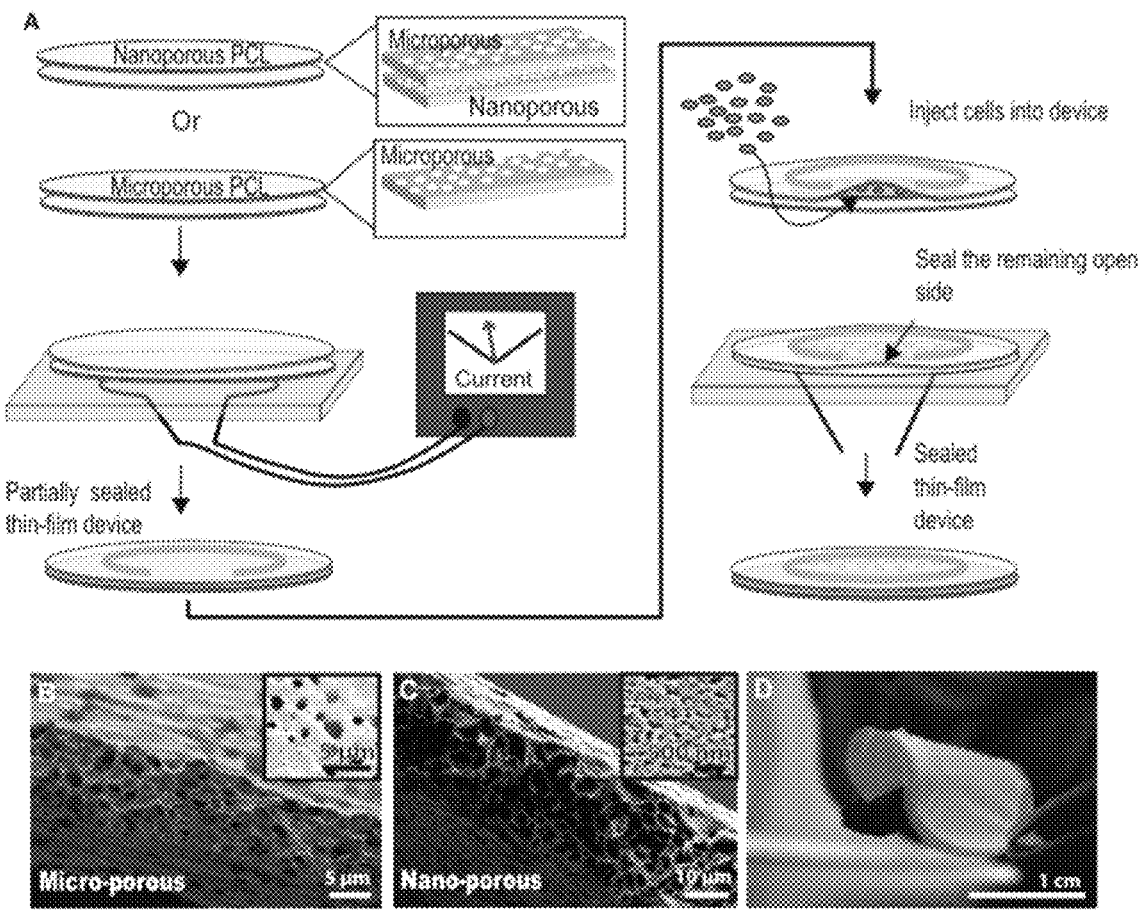
FIG. 1. PCL micro- and nano-porous thin-film fabrication for cell encapsulating devices. Panel A) Schematic of the device two-step heat-sealing and cell encapsulation. Panel B) Cross section SEM of the micro-porous thin-film and (inset) top down image of the film surface. Panel C) Cross-section SEM of the nano-porous thin-film and (inset) top-down image of the nano-porous film surface. Panel D) Image of an assembled device, demonstrating device flexibility.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

"Subject" refers to any animal, e.g., a mammal, such as a mouse, rat, goat, dog, pig, monkey, non-human primate, or a human.

"Biocompatible," as used herein, refers to a property of a material that allows for prolonged contact with a tissue in a subject without causing toxicity or significant damage.

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

"Therapeutically effective amount" refers to an amount effective, at dosages and for periods of time necessary, to achieve the desired therapeutic result.

"Tubing" or "tube", as used herein refers to an elongated structure having a cylindrical wall defining an interior space. A tubing can have a substantially constant inner diameter along the length of the tubing. The length of the elongated structure may be longer than the width by a factor of 5, 10, 20 or more.

An "end," as used in reference to an end of a tubing, is meant to indicate an extremity or an extreme portion of the tubing. The end of a tubing does not necessarily refer to a physical termination of the tubing, although the end of the tubing may in some cases coincide with a physical break in the tubing, depending on context.

The "internal volume," as used in reference to a tubing, refers to the volume of the space in the tubing bound by the internal wall.

"Lumen" as used in the context of the device of the present disclosure refers to the space or internal volume created by sealing the first and second layers around the edges of the device, wherein the layers are typically porous.

The terms "layer", "film", or "membrane" and plurals thereof as used in the context of a device of the present disclosure refer to the individual layers of the device that are typically formed from a polymer. The "layer", "film", or "membrane" used to manufacture a porous device of the present disclosure is typically porous and can be nanoporous or microporous. The phrases "nanoporous layer," "nanopore layer," "nanoporous membrane," "nanopore membrane," "nanoporous film," and "nanopore film" are used interchangeably and all refer to a polymer layer in which nanopores have been created. A nanoporous layer may include a backing or a supporting layer for structural support. The backing may be a microporous layer. The phrases "microporous layer," "micropore layer," "microporous membrane," "micropore membrane," "microporous film," and "micropore film" are used interchangeably and all refer to a polymer layer in which micropores have been created.

"Encapsulated" as used in the context of cells disposed in a lumen of the devices provided herein refers to cells that are contained within the device in the lumen defined between a first and second layer of the device.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the device" includes reference to one or more devices, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As summarized above, a thin film device for transplantation of a population of cells into a subject is provided. Also described herein are methods for making the device and methods for using such a device.

Device for Transplantation of Cells and Methods of Use

In certain embodiments, a device for transplantation of an encapsulated population of cells into the body of a subject may include a first nanoporous or microporous polymer layer, a second nanoporous or microporous polymer layer, wherein the first and second layers are in contact with each other along a periphery of the first and second layers thereby defining an enclosed space or a lumen between the first and second layers; and a population of cells disposed in the lumen between the first and second layers.

The device is configured to induce minimal foreign body response and to promote vascularization into the device. The porous material of the thin film device allows exchange of molecules (e.g., diffusion of oxygen, nutrients, cell metabolism waste products, therapeutic proteins) via the pores but is substantially impermeable to cells and to large proteins such as immunoglobulins and limits the transport of smaller proteins, such, as cytokines through the pores. Thus, the devices disclosed herein isolate the cells present in the lumen of the device from the immune system of the subject but allow exchange of smaller molecules supporting the viability and function of the transplanted cells.

When an implantable device containing cells has been isolated from the immune system by encasing it in a cell-impermeable layer, the implantable device often stimulates a local inflammatory response, called the foreign body response (FBR) that has long been recognized as limiting the function of implanted devices that require solute transport. FBR has been well described in the literature and is composed of three main layers. The innermost FBR layer, adjacent to an implanted device is composed of macrophages and foreign body giant cells. These cells form a monolayer of closely opposed cells over the surface of an implanted device. The intermediate FBR layer, lying distal to the first layer with respect to the device, is a wide zone (30-100 microns) composed primarily of fibroblasts and fibrous matrix. The outermost FBR layer is loose connective granular tissue containing new blood vessels. Upon induction of a FBR, an implanted device is isolated from the in vivo environment limiting the exchange of molecules with the implanted device, limiting the utility of the implanted device as well as, leading to the death of any cells provided within the implanted device.

The devices disclosed herein do not induce a significant FBR as evidenced by lack of fibrosis around the implanted devices of the present disclosure and by the viability of the cells in the device for a prolonged period of time.

The devices disclosed herein support viability of cells present in the lumen of the device upon transplantation into a subject, for at least one month, at least 2 months, 3 months, 4 months, 5 months, 6 months, 7 months, 8 months, 9 months, 10 months, 11 months, 12 months, 2 years, 3 years, 4 years, 5 years or longer.

The device of the present disclosure is substantially impermeable to cells such that cells do not cross the first and second polymer layers in detectable numbers. The device of the present disclosure is substantially impermeable to immunoglobulins such that the concentration of any immunoglobulins that gain access to the lumen of the device is below the level needed for an immune response against the cells present inside the lumen of the device. The device of the present disclosure substantially limits cytokines from entering the lumen of the device such that the concentration of cytokines that gain access to the lumen of the device is below the level required for an immune response against the cells present inside the lumen of the device.

The devices disclosed herein are typically planar and can have any two dimensional planar shape. In certain embodiments, the device may be circular, elliptical, square, rectangular, or a combination thereof. In some embodiments, the device may be substantially circular and may have a diameter between 1 cm and 5 cm.

In certain embodiments, the device may include an additional layer for increasing the rigidity of the device. For example, the device may include a layer of material disposed along a side edge of the device. The additional layer may facilitate maintenance of the device as a substantially planar device by preventing folding of the device during placement in a subject and/or after placement in a subject. The layer of material may be the same material as used for the first layer or the second layer or may be of a different material.

In certain embodiments, the device may be sealed entirely along the edges of the device thereby forming a completely enclosed internal space or lumen. In other embodiments, the device may be open at one or more locations at an edge of the device allowing access to the internal space or lumen of the device. When the device includes two openings into the lumen of the device the two openings may be located opposite each other, such as, on opposite sides of the planar device.

In certain embodiments, the device may include a lumen having one or more openings at which the first and second polymer layers are not sealed together. The device may further include a tubing inserted into the opening. In certain embodiments, the tubing may be affixed to the device by sealing the first and second layers, at the opening, to the exterior wall of the tubing. In certain embodiments, a first end of the tubing may be placed at the opening and positioned in the lumen such that a minimal volume of the lumen is taken up by the tubing while allowing loading of fluids into the lumen of the device. The second end of the tubing, which is distal to the first end may be used as a port for introducing fluids into the lumen via the tubing.

In certain embodiments, the device may include two openings at which the first and second layers are not sealed together thereby defining a lumen with two openings. Each of the openings may include a tubing placed at the openings.

The first opening may be used as an ingress port for introducing a fluid (e.g., a cell medium containing cells) into the lumen of the device and the second opening may be used as an egress port for removing fluids (e.g., fluid containing dead cells, cell debris, etc.) from the lumen of the device. As noted herein, the length of the tubing placed within the lumen may be held at a minimal to maximize the volume available for the population of cells in the lumen. The tubing may be affixed to the device by sealing the first and second layers of the device to the exterior wall of the tubing at the first ends of each of the tubings. The second end of the tubing forming one or more access ports into the lumen of the device may be closed when not being used to access the interior of the lumen. The second end(s) may be closed by forming a plug at the second end(s). In certain cases, the plug may be a silicone plug.

The length of the tubing may be selected based on a number of factors. For example, a shorter tubing may be used when loading a population of cells into the lumen of the device ex vivo, for example, prior to placement of the device into a subject. A longer tubing may be used if the tubing is to be used for introducing fluids into and/or removing fluids from the lumen of the device after placement of the device into a subject.

In certain cases, the device may include first and second polymer layers that are sealed to each other along the edges other than at two locations creating a lumen defined by the sealed edges and having two openings. A first end of a first tubing may be placed at a first of the two openings. A first end of a second tubing may be placed at a second of the two openings. The first ends of the first and second tubing may be affixed to the device by sealing the first layer and the second layer to the exterior wall of the device, such that the lumen is sealed around the exterior wall of the tubing(s). The second ends of the first and second tubing may be connected to a remote fill port which converts the device into a refillable, closed system. The remote fill port may contain a solid detectable backing, which allows for, e.g., percutaneous locating of the port with a magnet finder if the backing is magnetic. The remote fill port may include two separate chambers in the port for access to the second end of the first tubing and the second end of the second tubing. In certain cases, the tubing may be, e.g., Silastic® silicone tubing. The port may also contain suture tabs at its base to allow for suturing to soft tissue upon implantation, thus helping resist turning or movement of the port. An exemplary remote fill port is described in WO 2016/028774, which is herein incorporated by reference in its entirety.

In certain embodiments, the device and/or the population of cells in the device may be amenable to visualization after placement of the device into the subject. For example, the device and/or cells may be fluorescent and as such may be visualized by imaging a portion of the body of the subject into which the device is placed. A fluorescent device may facilitate removal of the device and/or access to the tubing of the device if the device is placed wholly inside a subject.

As noted herein, the device may include a first layer that may be nanoporous or microporous and a second layer that may be nanoporous or microporous. The microporous and/or the nanoporous layer may be formed as described in U.S. Patent Application Publication No. 20140170204, which is herein incorporated by reference in its entirety.

In certain embodiments, the first and/or the second layer of the device may be microporous. The pore diameter in the microporous layer may range from 1 µm to 5 µm, such as, 1 µm to 4.5 µm, 1 µm to 3.5 µm, 1 µm to 2.5 µm, 1 µm to 2 µm, 1.5 µm to 3 µm, 1.5 µm to 2.5 µm, 1.5 µm to 3 µm, 1.5 µm to 5 µm, e.g., 1 µm, 2 µm, or 3 µm. As explained herein, the pores in a microporous layer may be created by forming a layer that includes a polymer that is water insoluble and a pore forming agent that is a water-soluble polymer. The pore forming agent forms spheres in the water insoluble polymer layer which spheres are dispersed along the width of the water insoluble polymer layer as well as across the thickness of the water insoluble polymer layer. The spheres determine the pore diameter and a plurality of spheres when connected across the thickness of the water insoluble polymer layer (cross-section of the water insoluble polymer layer) provide a continuous channel across the water insoluble polymer layer upon dissolution of the spheres. For the formation of a microporous layer, the spheres of the water soluble polymer are dissolved by exposing the layer to an aqueous solution, thereby creating spaces/holes throughout the microporous membrane. The spaces/holes may have a diameter of about 1 µm to 5 µm. A series of spaces/holes may be present sequentially across the thickness of the water insoluble polymer layer and interconnected to provide a channel which channel may have a varying diameter. For example, a region in the channel at which two spaces are connected (e.g., where two spheres of the pore forming agent were in contact with each other and dissolved to provide two spaces connected to each other) may have a smaller channel diameter than the other regions in the channel. The smallest diameter of the channel may be referred to as the connectivity diameter. In certain embodiments, the connectivity diameter may range from 900 nm-100 nm, such as, 900 nm-150 nm, 900 nm-200 nm, 700 nm-100 nm, 700 nm-150 nm, 700 nm-200 nm, 500 nm-100 nm, 500 nm-150 nm, 300 nm-100 nm, 300 nm-150 nm, or 300 nm-200 nm.

In certain embodiments, the first and/or the second layer of the device may be nanoporous. The pore diameter in the nanoporous layer may range from 10-300 nm, such as, 20-300 nm, 30-300 nm, 10-200 nm, 20-200 nm, 30-200 nm, 10-100 nm, 20-100 nm, 30-100 nm, 30-50 nm, 30-40 nm, 20-250 nm, 20-150 nm, or 25-150 nm, e.g., 30 nm, 50 nm, 100 nm, 150 nm, or 300 nm. In certain embodiments, the nanopore layer may include a backing layer to structurally support the nanopore layer. In certain embodiments, the backing layer may be a microporous layer, such as a microporous layer described herein.

In certain embodiments, the first and/or the second layer of the device may have a % porosity of at least 50%, such as, at least 55%, at least 60%, at least 65%, or at least 70%, e.g., from 50% to 70%, 55% to 70%, or 55% to 65%. % porosity of the first and second nanoporous polymer layers of the device may be controlled by the number of nanorods use for the fabrication of the layer. Similarly, % porosity of the first and second microporous polymer layers of the device may be controlled by the amount of pore forming agent (e.g., a water soluble polymer) used during manufacture of the microporous polymer layer.

As noted herein, the device is a thin layer device where the individual first and second layers of the device are each less than 30 µm in thickness. As such, the first and second layers are less than 30 µm thick, such as, less than 25 µm, 20 µm, 15 µm, 10 µm, or 5 µm, e.g., 20 µm-10 µm, 25 µm-5 µm, 20 µm-5 µm, 15 µm-5 µm, 15 µm-10 µm, 13-10 µm, 13 µm-8 µm, 12 µm-8 µm, 11 µm-9 µm, 10 µm±5% in thickness.

In certain embodiments, the entire device is less than 60 µm thick and has a surface area of 0.5 $cm^2$ to 5 $cm^2$, such as, a surface area larger than 0.75 $cm^2$, larger than 1 $cm^2$, larger than 1.5 $cm^2$, larger than 2 $cm^2$, larger than 2.5 $cm^2$, larger than 3 $cm^2$, larger than 3.5 $cm^2$, larger than 4 $cm^2$, larger than 4.5 cm², and up to 5 cm². The device may include a first layer and a second layer. Both layers may be microporous or nanoporous. The diameter of the pores in the microporous polymer layers ranges from 1 to 5 µm with a connectivity diameter in the range as noted herein. The diameter of the pores in the nanoporous polymer layer ranges from 10 nm to 300 nm, such as, 20-300 nm, 30-300 nm, 10-200 nm, 10-50 nm, 20-200 nm, 30-200 nm, 10-100 nm, 20-100 nm, 30-100 nm, 20-250 nm, 20-150 nm, or 25-150 nm, e.g., 20 nm, 30 nm, 50 nm, 100 nm, 150 nm, or 300 nm.

In certain embodiments, the entire device is less than 50 µm thick and has a surface area of 0.75 cm² to 4.5 cm² per side. The diameter of the pores in the microporous polymer layers ranges from 1 µm to 3 µm, where the connectivity diameter of the pores (diameter of a through channel) may range from 900 nm-100 nm, such as, 900 nm-150 nm, 900 nm-200 nm, 700 nm-100 nm, 700 nm-150 nm, 700 nm-200 nm, 500 nm-100 nm, 500 nm-150 nm, 300 nm-100 nm, 300 nm-150 nm, or 300 nm-200 nm. The diameter of the pores in the nanoporous polymer layers ranges from 20 nm to 100 nm, such as, 40-100 nm, 30-50 nm, 20-50 nm, or 25-100 nm, e.g., 20 nm, 30 nm, 50 nm, or 100 nm.

In certain embodiments, the entire device is less than 40 µm thick and has a surface area of 1 cm² to 4 cm² per side. The size of the pores in the microporous polymer layer ranges from 1 µm to 3 µm with a connectivity diameter in the range as noted herein. The size of the pores in the nanoporous polymer layers ranges from 25 nm to 100 nm, such as, 25-75 nm, 30-50 nm, 25-50 nm, or 25-40 nm, e.g., 25 nm, 30 nm, 50 nm, or 100 nm.

In certain embodiments, the entire device is less than 30 µm thick and has a surface area of 1 cm² to 2 cm² per side. The diameter of the pores in the microporous polymer layer ranges from 1 µm to 3 µm with a connectivity diameter in the range as noted herein. The diameter of the pores in the nanoporous polymer layers ranges from 30 nm to 100 nm, such as, 30-75 nm, 30-50 nm, 40-100 nm, 40-75 nm, 40-50 nm, 50-100 nm, or 50-75 nm, e.g., 30 nm, 40 nm, 50 nm, 60 nm, or 80 nm. For example, the first and second layers may each be 10 µm±3 µm thick. In certain embodiments, the first layer may be microporous and the second layer may be nanoporous or vice versa.

In certain embodiments, the device includes a first layer and a second layer, each of which are each 10 µm±3 µm thick, wherein the entire device has a surface area of 1 cm² to 2 cm² per side. The first layer and the second layer are nanoporous and diameter of the pores in the nanoporous polymer layers ranges from 30 nm to 100 nm, such as, 30-75 nm, 30-50 nm, 40-100 nm, 40-75 nm, 40-50 nm, 50-100 nm, or 50-75 nm, e.g., 30 nm, 40 nm, 50 nm, 60 nm, or 80 nm. In other embodiments, first layer and the second layer are microporous and the diameter of the pores in the microporous polymer layer ranges from 1 µm to 3 µm (e.g., 2 µm±0.5 µm diameter) with a connectivity diameter ranging from 900 nm-100 nm, such as, 900 nm-150 nm, 900 nm-200 nm, 700 nm-100 nm, 700 nm-150 nm, 700 nm-200 nm, 500 nm-100 nm, 500 nm-150 nm, 300 nm-100 nm, 300 nm-150 nm, or 300 nm-200 nm.

The devices of the present disclosure are configured to prevent immune cells from entering the lumen of the device and substantially inhibit antibodies and cytokines from entering the lumen while promoting nutrient exchange with the encapsulated cells and release of therapeutic proteins secreted by the encapsulated cells as well as diffusion of metabolic waste products out of the device. The pores and the thickness of the thin layers forming the thin film device of the present disclosure are configured to permit passage of small molecules, such as salts, sugars, amino acids, dopamine, glucose, insulin and substantially inhibit passage of large molecules such as, antibodies, C3b, cytokines (e.g., interferons, interleukins, tumor necrosis factors, and the like) and of cells. The first and second porous polymer layers are configured to allow exchange of small molecules that have a molecular weight less than 10 kDa and/or a hydrodynamic radius of less than 2 nm. The first and second porous polymer layers are configured to substantially limit large molecules that have a molecular weight greater than 15 kDa and/or a hydrodynamic radius of greater than 2 nm from crossing the layers and entering the lumen of the device.

Any polymer material may be used to form the first and second porous layers of the devices disclosed herein. Representative polymers include methacrylate polymers, polyethylene-imine and dextran sulfate, poly(vinylsiloxane) ecopolymerepolyethyleneimine, phosphorylcholine, poly(ethyl methacrylate), polyurethane, poly(ethylene glycol), poly (lactic-glycolic acid), hydroxyapetite, poly(lactic acid), polyhydroxyvalerte and copolymers, polyhydroxybutyrate and copolymers, polycaprolactone, polydiaxanone, polyanhydrides, polycyanocrylates, poly(amino acids), poly(orthoesters), polyesters, collagen, gelatin, cellulose polymers, chitosans, and alginates or combinations thereof. Additional examples that may be used to coat the scaffold include but are not limited to: collagen, fibronectin, extracellular matrix proteins, vinculin, agar, and agarose. It should be understood that various mixture of the polymers may be used.

In certain embodiments, the first layer and/or the second layer may be formed from poly(caprolactone) (PCL). The PCL used for forming the first and/or the second layer may have a number average molecular weight (Mn) higher than 50 kDa, such as, higher than 55 kDa, 60 kDa, 65 kDa, or 70 kDa, and up to 200 kDa, e.g., 50-200 kDa, 55-200 kDa, 60-200 kDa, 65-200 kDa, 70-200 kDa, 50-150 kDa, 55-150 kDa, 60-150 kDa, 65-150 kDa, 70-150 kDa, 50-100 kDa, 55-100 kDa, 60-100 kDa, 65-100 kDa, 70-100 kDa, 50-90 kDa, 55-90 kDa, 60-90 kDa, 65-90 kDa, or 70-90 kDa. Furthermore, the molecular weight of the PCL polymer may be selected based on the duration for which the device is to be maintained in the body of a subject without substantial degradation of the polymer.

Under physiological conditions, a biodegradable polymer such as PCL polymer degrades by random chain scission, which gives rise to a two-phase degradation. Initially, as molecular weight decreases the physical structure is not significantly affected. Degradation takes place throughout the polymer material, and proceeds until a critical molecular weight is reached, when degradation products become small enough to be solubilized. At this point, the structure starts to become significantly more porous and hydrated. In certain cases, a higher molecular weight polymer may be used when the device is to be used for providing transplanted cells into the subject for at least one year. For example, when the device is to maintain the integrity of the porous polymer layers for at least one year, the porous polymer layers may be made from a polymer, that has at least 70 kDa Mn, e.g., at least 75 kDa Mn, at least 80 kDa Mn, or at least 85 kDa Mn, or at least 90 kDa Mn, and up to 100 kDa Mn. In embodiments where the device is configured to degrade by 6 months, the first and second porous polymer layers may be formed from a lower molecular weight polymer, such as, a polymer having Mn of 10-20 kDa.

In some embodiments, the biodegradable polymer includes a blend of polymers where the polymers may be of the same or a different type of polymer, and each polymer may be of a different MW. In some embodiments, the biodegradable polymer includes a blend of a high MW polymer and a low MW polymer. The high MW polymer may be of about 25 kDa or more, such as about 30 kDa or more, about 40 kDa or more, about 50 kDa or more, about 60 kDa or more, about 70 kDa or more, about 80 kDa or more, about 90 kDa or more, or about 100 kDa, and up to 150 kDa. The low MW polymer may be of about 20 kDa or less, such as about 15 kDa or less, about 10 kDa or less, about 8 kDa or less, about 6 kDa or less, and down to 4 kDa.

In some embodiments, the ratio by mass of the high MW polymer to the low MW polymer in a blend of polymers is between about 1:9 and about 9:1, such as between about 2:8 and about 8:2, between about 2:8 and about 6:4, or between about 2:8 and about 1:1. In certain embodiments, the ratio by mass of the high MW polymer to the low MW polymer is about 3:17, about 2:8, about 1:3, about 3:7, about 7:13, about 2:3, about 9:11, about 1:1, about 11:9, or about 3:2.

In certain embodiments, thin film devices for transplantation of cells into the body of a subject do not comprise poly(lactic-co-glycolic acid) (PLGA), polyvinylidene difluoride (PVDF), alginate, collagen, gelatin, agarose, silicon, cellulose phosphate, or polypropylene (PP).

In certain embodiments, the exterior surface of the device may be modified by disposing one or more agents that improve the device. For example, molecule that promotes vascularization of the device or inhibits immune or inflammatory response to the device may be disposed on the exterior of the device. Such molecules include, but are not limited to VEGF (vascular endothelial growth factor), PDGF (platelet-derived growth factor), FGF-1 (fibroblast growth factor), angiopoietin MCP-1, $\alpha v\beta 3$, $\alpha v\beta 5$, CD-31, VE-cadherin, ephrin, plasminogen activators, angiogenin, Del-1, aFGF (acid fibroblast growth factor), vFGF (basic fibroblast growth factor), follistatin, G-CSF (granulocyte colony-stimulating factor), HGF (hepatocyte growth factor), Leptin, placental growth factor, PD-ECGF (platelet-derived endothelial growth factor), and the like.

The devices of the present disclosure are used to provide encapsulated cells in a subject. The method for providing the encapsulated cells includes providing a thin film device, e.g., a multilayer thin film device, as provided herein, transplanting the thin film device into the subject, promoting vascularization into the lumen of the device via the pores in the first polymer layer and/or second polymer layer; limiting foreign body response to the device; limiting ingress of cells, immunoglobulins, and cytokines into the lumen via the first and the second polymer layers; and releasing from the first polymer layer and/or the second polymer layer molecules secreted by the population of cells. The devices disclosed herein may promote vascularization into the lumen of the device such that at least 20% of the device is vascularized within a month after transplantation into a subject, such as at least a 30% vascularization, 40% vascularization, 50% vascularization, 60% vascularization within a month after transplantation into a subject. The devices disclosed herein may limit the diffusion of cytokines and immunoglobulins through the pores in the first polymer layer and second polymer layer such that the diffusion rate is less than 50%, less than 40%, less than 30%, less than 20% compared to diffusion in absence of a barrier layer.

The devices of the present disclosure are sized to house an effective number for transplanted cells for treatment of a subject in need thereof. For example, the subject may be suffering from a condition caused by lack of functional cells, e.g., wherein molecules typically secreted by functional cells are not secreted or are secreted at a level resulting in the condition. Providing functional cells could alleviate the condition. Exemplary conditions include type 1 diabetes, Parkinson's disease, muscular dystrophy and the like.

The device may be transplanted into any suitable location in the body, such as, subcutaneously, intraperitoneally, or in the brain, spinal cord, pancreas, liver, uterus, skin, bladder, kidney, muscle and the like. The site of implantation may be selected based on the diseased/injured tissue that requires treatment. For treatment of a disease such as diabetes mellitus (DM), the device may be placed in a clinically convenient site such as the subcutaneous space or the omentum.

Populations of cells for transplantation using the devices described herein include but are not limited to, bone marrow cells; mesenchymal stem cells, stromal cells, pluripotent stem cells (e.g., induced pluripotent stem cells and embryonic stem cells), blood vessel cells, precursor cells derived from adipose tissue, bone marrow derived progenitor cells, intestinal cells, islets, Sertoli cells, beta cells, progenitors of islets, progenitors of beta cells, peripheral blood progenitor cells, stem cells isolated from adult tissue, retinal progenitor cells, cardiac progenitor cells, osteoprogenitor cells, neuronal progenitor cells, and genetically transformed cells, or a combination thereof. The encapsulated cells may be from the subject (autologous cells), from another donor (allogeneic cells) or from other species (xenogeneic cells). The cells can be introduced into the lumen of the device and the device may be immediately (within a day) implanted into a subject or the cells may cultured for longer period, e.g. greater than one day, to allow for cell proliferation prior to implantation. The number of cells introduced into the lumen of the device may vary and may be determined empirically.

In certain embodiments, the devices disclosed herein may be used to treat a person having diabetes, such as, type 1 diabetes. The device may include pancreatic islet cells or may include stem cells that are capable of differentiating into pancreatic islet cells. In certain embodiments, pluripotent stem cells (PSCs) may be differentiated into pancreatic islet cells inside the device and then the device containing the differentiated pancreatic islet cells is placed in the subject (e.g., in the omentum, adjacent to pancreas or liver). In some case, the device may include PSCs and the device may be implanted adjacent the pancreas or liver of the subject.

As noted herein, the devices disclosed herein may maintain the transplanted cells in a functional and viable state for at least 1 month and up to a period of at least 2 months, 3 months, 4 months, 5 months, 6 months, 7 months, 8 months, 9 months, 10 months, 11 months, or up to a year or longer. In certain cases, the integrity of the device is maintained for at least one year and the cells in the device may be replaced with a fresh population of cells using the tubing attached to the device (e.g., via a remote fill port) while the device is located inside a subject.

The methods and devices disclosed herein can be used for both human clinical and veterinary applications. Thus, the subject or patient to whom the device is administered can be a human or, in the case of veterinary applications, can be a laboratory, agricultural, domestic, or wild animal. The subject devices and methods can be applied to animals including, but not limited to, humans, laboratory animals such as monkeys and chimpanzees, domestic animals such as dogs and cats, agricultural animals such as cows, horses, pigs, sheep, goats, and wild animals in captivity such as bears, pandas, lions, tigers, leopards, elephants, zebras, giraffes, gorillas, dolphins, and whales.

Methods of Preparation

Also provided are methods of preparing the subject devices. In some embodiments, the method includes obtaining or fabricating a first microporous or nanoporous polymer layer and a second microporous or nanoporous polymer layer, where the first and second layers are similarly sized. The first layer has a first surface and a second surface opposite the first surface. The second layer also has a first surface and a second surface opposite the first surface. The method further comprises positioning the second layer over the first layer such that the edges of the layers are aligned and the second surface of the second layer is in facing configuration with the first surface of the first layer. The method further comprises sealing the second surface of the second layer to the first surface of the first layer. The seal may be formed along a side edge of the first and second layers forming an enclosed space or lumen in between the second surface of the second layer and the first surface of the first layer. The seal may initially be formed along the side edges of the first and second polymer layers while leaving an unsealed edge. A population of cells may introduced into the lumen via the opening and the opening may then be closed by sealing the second surface of the second layer to the first surface of the first layer, thereby enclosing the population of cells inside the device.

Any method for obtaining or fabricating a microporous or nanoporous polymer layer may be used. For example, a microporous polymer layer and a nanoporous polymer layer may be fabricated using a method disclosed in US Patent Application Publication 20140170204, Steedman et al., *Biomedical Microdevices*, 12(3) (2010) 363-369, Bernards et al., *J. Ocul. Pharmacol. Ther.* 2013, 29, 249-257; Bernards et al., *Adv. Mater.* 2010, 22, 2358-2362; or Bernards et al., *Nano Lett.* 2012, 12, 5355-5361, each of which is herein incorporated by reference in its entirety.

In certain embodiments, the population of cells may be loaded into the lumen via an opening. In other embodiments, a tubing may be inserted into the opening and used to load the population of cells into the lumen. In certain cases, the tubing may be retracted from the opening and the opening sealed after the population of cells has been introduced into the lumen.

In certain embodiments, the tubing inserted into the opening may be affixed to the device by sealing the second surface of the second layer and the first surface of the first layer to the exterior wall of the tube.

In certain embodiments, the seal may initially be formed along the side edges of the first and second polymer layers while leaving unsealed edges at two locations, thereby providing a first and a second opening into the lumen. A first end of a first tubing may be inserted into the first opening and the tubing fixed in place by sealing the first and second layers to the exterior wall of the tubing. A first end of a second tubing may be inserted into the second opening and the tubing fixed in place by sealing the first and second layers to the exterior wall of the tubing. The second ends of each tubing may be configured for attachment to a remote fill port for forming a refillable, closed system, e.g., after the in vivo placement of the device, the second end of each the tubing may be attached to a remote fill port, such as a remote fill port described in WO 2016/028774.

Sealing of the first and second layers to each other or to a tubing may be carried out using an adhesive, or by using heat, or a solvent to melt the layers. Sealing of the two layers may be at the outermost edge of the layers or at a location adjacent to the outermost edge of the layers.

In some embodiments, the device may include a third polymer layer disposed along the edges of the device to provide a thicker edge to the device. This third polymer layer may be disposed along the entire edge of the device or on a portion thereof. The portion of the edge of the device to be covered by the third polymer layer may be determined by the in vivo location at which the device is to be disposed. The third layer may be affixed to the edge of the device via use of an adhesive, heat, or a solvent to melt the layers together. The third layer may be a nonporous polymer layer or a microporous polymer layer. The third layer may have a thickness of at least 10 µm, such as, at least 30 µm, 100 µm, 300 µm, 500 µm, 1 mm, or 2 mm or higher, e.g., 100 µm-2 mm, 300 µm-2 mm, 500 µm-2 mm, or 1 mm-2 mm.

In embodiments, where nanoporous polymer layers are used to fabricate the device, the nanoporous layer may include a microporous backing layer. The microporous polymer layer used for structurally supporting the nanoporous polymer layer may be made from the same polymer as the nanoporous layer. The microporous polymer layer is applied to the nanoporous layer such that the two layers are in contact with each other across a surface of the two layers. The nanoporous layer with the microporous backing may be used in either orientation when forming the device.

In certain embodiments, the sealing is performed using an annulus that may be heated. An exemplary method includes the use of U-shaped wire that is heated to a temperature (e.g., 80° C.) above the melting temperature of the polymers (e.g., PCL) used in the fabrication of the device. The wire may be placed underneath the two layers and heated thereby melting the two layers at the locations adjacent the wire. In some examples, the first and second porous polymer layer may be placed over a U-shaped nichrome wire embedded in PDMS (Sylgard 184). The diameter of the wire may be selected based on the desired volume of the lumen. To secure the first and second layers a weight (e.g., PDMS weight) may be placed over the first and second layers holding them flat. A current may then be applied to the wire for melting the layers and defining the lumen shape and leaving an opening. The size and shape of the wire may be selected to produce devices of a desired size. Subsequent to loading of the cells into the lumen the open side of the device may be closed.

In certain embodiments, the sealing step of the subject methods is performed using a laser beam to heat a defined area of the thin film layers, for example, a circular area surrounding the area where the cells are to disposed. In certain embodiments, the sealing step of the subject methods is performed by disposing an adhesive material on one or both of the first and second layers. For example, an adhesive material may be disposed on the first layer and/or the second layer in an area surrounding the area where the lumen is to be created. The adhesive may seal the two layers when the two layers are brought in contact. Alternatively, the adhesive may be a heat sensitive adhesive or a pressure sensitive adhesive. In these embodiments, heat or pressure may be applied in order to seal the layers of the thin film device. It will be understood by those of skill in the art that any method effective to seal the first and second layers to each other or to a tubing may be used in making the devices described herein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods:

Chemicals were purchased from Sigma Aldrich unless noted and cell culture materials were purchased from the University of California, San Francisco (UCSF) cell culture facility. All films were spuncast onto silicon wafers at 1000 rpm for 30 seconds followed by 2000 rpm for 30 seconds. Devices were characterized with a Carl Zeiss Ultra 55 Field-Emission Scanning Electron Microscope using an in-lens Secondary Electron detector.

Micro-Porous Thin-Film Fabrication

Micro-porous PCL thin-films were spuncast from a solution of 150 mg/mL PCL (70-90 kDa Mn) and polyethylene glycol (PEG, 2 kDa Mn) in 2,2,2-trifluoroethanol, which was prepared by stirring at 65° C. until dissolved. Following spin-casting, the PEG was dissolved by soaking in water for 1 hour, resulting in micro-porous PCL films with pores approximately 2 µm in diameter. Devices were 1 cm in diameter resulting in a surface area of 1.57 cm$^2$ per side, with 67.5±1.3% porosity and 0.37±0.02 density.

Nano-Porous Thin-Film Fabrication

Nano-porous PCL films were formed using an established template-based approach reported elsewhere (Bernards, D. A. and Desai, T. A., Adv. Mater. 2010, 22, 2358-2362). In brief, a 0.5 M solution of zinc acetate dihydrate and ethanolamine in 2-methoxyethanol was spuncast onto silicon wafers and annealed at 300° C. on a hot plate to generate a zinc oxide (ZnO) seed layer. From this seed layer, ZnO nanorods were hydrothermally grown in a 5 mM zinc acetate solution at 85-90° C. for two hours. A 150 mg/mL PCL solution was then spuncast onto the nanorods followed by a 150 mg/mL PEG:PCL solution to provide a micro-porous support, creating a nano-porous film with a micro-porous backing support layer. The film was soaked in a dilute sulfuric acid solution to etch away the ZnO nanorods and also dissolve the PEG, resulting in a nano-porous membrane with pores ranging from 30 nm to 100 nm supported by a micro-porous backing. Membrane characterizations and ZnO nanorod morphology were previously measured (Bernards et al., J. Ocul. Pharmacol. Ther. 2013, 29, 249-257; Bernards et al., Adv. Mater. 2010, 22, 2358-2362; Bernards et al., Nano Lett. 2012, 12, 5355-5361).

Non-Porous Membrane Fabrication

Non-porous PCL films were spuncast from a solution of 150 mg/mL PCL (70-80 kDa Mn) in 2,2,2-trifluoroethanol, which was prepared by stirring at 65° C. until dissolved. Non-porous poly(lactic-co-glycolic acid) (PLGA) films were spun cast from a solution of 300 mg/mL PLGA (85:15 LA:GA 45 kDa Mn) in 2,2,2-trifluoroethanol. Polyvinylidene fluoride (PVDF) film was prefabricated from Sigma and cut to shape.

Assembly of Thin-Film Devices

Devices consisted of two PCL thin-films heat-sealed together using resistive heating of a nichrome wire. A two-step heat-sealing method was used where 1.2 Amp current ran through a nichrome wire outlining the regions to be sealed. For the first sealing step, two films were placed over a U-shaped nichrome wire embedded in PDMS (Sylgard 184), 1 cm in diameter. To secure the membranes a PDMS weight was placed over the films, holding them flat. A 1.2 Amp current ran through the wire for 30 seconds and sealed the devices in the shape of a U, defining the device lumen shape and leaving an open side for cell injection. 1.5 Million MIN6 cells in high glucose Dulbecco's Modified Eagle's (DME) were injected into the devices through the remaining open side. Second, the remaining side of the device was sealed by placing the open edge over a straight nichrome wire embedded in PDMS and heat-sealed with a 1.2 Amp current for 30 seconds.

Characterization Using Scanning Electron Microscopy of Films and Devices

Micro- and nano-porous thin PCL films were mounted on a flat SEM mount with colloidal graphite (Ted Pella, Inc.). Cross sections were flash-dipped in isopropanol followed by liquid nitrogen freeze fracture and then mounted. Devices from in vivo experiments were fixed with 3.7% formaldehyde for 30 minutes, washed in deionized water three times, then sequentially dehydrated in increasing ethanol concentrations and mounted.

Cell Culture

MIN6 cells were cultured using standard media conditions (Miyazaki, et al., Endocrinology 1990, 127). Genes for mCherry and puromycin resistance were introduced using a lentivirus construct designed by the Lentiviral Core at UCSF. The cells were transduced using standard protocol with a multiplicity of infection of 2, and transduced cells were selected using puromycin. Genes encoding firefly luciferase and green fluorescence protein were similarly introduced into MIN6 cells. Primary islets were isolated by the Islet Core at UCSF using standard islet isolation protocols (Szot et al., J. Vis. Exp. 2007, 1640, 255).

Glucose Stimulated Insulin Secretion

Insulin secretion was analyzed using a glucose-stimulated insulin secretion assay. Cells were rested for 30 minutes in medium-containing 5 mM glucose and then stimulated using medium-containing 15 mM glucose. Culture supernatant was collected at 30 minutes and 60 minutes after addition of high glucose. Insulin protein content in the culture supernatant was measured using an enzyme linked immunosorbant assay (Mercodia). The ratio of insulin secreted at high to low glucose conditions was used to calculate the glucose stimulation index.

Cytokine Assay

To determine the effect of cytokines on the viability of encapsulated beta cells, 250,000 cells in micro- or nano-porous devices were cultured in a cytokine cocktail consisting of TNFα (300 ng/mL; VWR), IL1β (110 ng/mL; VWR) and IFNγ (200 ng/mL; Fisher) in high glucose DME media, with 10% fetal bovine serum, 1% penicillin, and 1% streptomycin. The devices were imaged daily for the mCherry signal using a standard spectrophotometer. The signal intensity was measured for each respective device for 7 days, and normalized against the initial signal.

Bioluminescent Imaging

Thin-film devices with luciferase-expressing MING (MIN6.LUC) cells were implanted, in either the subcutaneous space on the dorsal aspect, the abdominal cavity between the muscle wall and the liver of MOD. Cg-Prkdc$^{scid}$ Ill2rg$^{tm1Wjl}$/SxJ (NSG) or BALB/C mice. Persistence of the encapsulated cells in vivo was assessed by monitoring luciferase activity using a Xenogene IVIS 200 imaging system (Perkin Elmer). The animals transplanted with MIN6.LUC cells, were injected IP with D-luciferin solution (Goldbio, St. Louis, Mo.) at the dose of 150 mg/kg 8 minutes before imaging in order to capture the peak in bioluminescent intensity, as previously described (Fowler et al., Transplantation 2005, 79, 768-776). The mice were anesthetized with an isoflurane mixture (2% in 98% O$_2$) and imaged by using a Xenogen IVIS 200 imaging system. Bioluminescent images were acquired for 1 minute and then analyzed using the Living Image analysis software (Xenogen Corp., Alameda, Calif.). Regions of interests (ROI) were centered over the bioluminescent regions. Photons were counted within the ROI over the acquisition time. Adherence to the same imaging protocol ensured consistent signal detection and allowed us to compare data acquired over a period of at least 3 months.

Histology

Mouse tissue samples were collected and fixed in 4% paraformaldehyde for 24 hours, washed with phosphate buffered saline at 4° C. for 48 hours, then 30% sucrose for 24 hours. Samples were then taken to the Mouse Pathology Core at UCSF and Optimal Cutting Temperature (OCT) embedded, sliced, and Hematoxylin- and Eosin-stained or Masson's-Trichrome-stained by either the Mouse Pathology Core or the Histology and Imaging Core at UCSF.

Vasculature

At 7, 14, 30, and 90 days after transplantation, PCL device-bearing mice were anesthetized with an intraperitoneal injection of Avertin solution 2.5% (Sigma) and subjected to optical imaging using a Leica MZ16F microscope (Leica Biosystems, Wetzlar, Germany). The animals were euthanized by cervical dislocation and the encapsulated devices were collected for further analysis. The images of the encapsulated grafts were analyzed using ImageJ software. Vessel density was measured by automated counting of red pixels divided the area of the ROI within the device; a threshold was previously set for the red channel to subtract background.

The present disclosure describes fabricated and characterized poly-caprolactone (PCL) thin-film macroencapsulation devices as an innovative strategy to address the challenges of existing micro- and macroencapsulation approaches. The thin compliant design allows diffusion and flexibility similar to microencapsulation approaches, while the device surface area allows precise membrane control and retrievability, features associated with larger macroencapsulation technologies. The studies described herein show that encapsulated cells demonstrated viability, function, protection from immune-cell intrusion, protection from cytokine-mediated cell death, and neovascularization. PCL has been used in FDA-approved medical devices and has demonstrated long-term biocompatibility in multiple animal models (Bernhardt et al., *Biomatter.* 2012, 2, 158-265; Bernards, D. A. and Desai, T. A. *Soft Mater.* 2011, 6, 1621-1631; Bernards et al. *J Ocul Pharmacol Ther.* 2013, 29, 249-257; Bernards, D. A. and Desai T. A. *Rev Adv Mater Sci.* 2010, 22, 2358-2362; Abedalwafa et al. *Rev Adv Mater Sci.* 2013, 34, 123-140; Angius et al., *Biomaterials* 2013, 33, 8034-8039). Additionally, PCL degradation can be tuned to match the lifetime of the encapsulated cells, eliminating the need for device removal (Bernards, et al., *Nano Lett.* 2012, 12, 5355-5361; Mendelsohn et al, *Langmuir.* 2010, 26, 9943-9949). The use of porous PCL thin films allows a thin and flexible device to be designed with either micro- or nanoscaled features leading to better nutrient exchange, precise membrane control, and device tracking. In this study, the MIN6 cell line, a well-established mouse insulinoma cell line known to respond to glucose with insulin secretion, was used as a model for islet beta cells. Using MIN6 cells provides a sustainable and consistent source of cells across experiments. Primary islets were also used to demonstrate long-term viability of encapsulated cells.

We describe the fabrication of micro-porous and nano-porous PCL thin-film cell-encapsulation devices, cell behavior in these devices, and in vivo integration of these devices in allogeneic mouse models. To design these encapsulation devices, the geometry was engineered to combine the advantages of the precise membrane control of macro-encapsulation devices with improved nutrient exchange of micro-encapsulation devices. Furthermore, the choice of PCL was based on its range of molecular weights, tunable degradation profile, flexibility, and use as a non-toxic material in FDA-approved medical devices. Two different methods were used to create micro- and nano-porous membranes for thin-film devices. The micro-porous films utilize phase separation of PEG and PCL in solution. In this method, after films are cast, the pore forming agent (PEG) is dissolved, leaving a micro-porous film (Bernards et al., *Nano Lett.* 2012, 12, 5355-5361). By tuning the concentration of ratio and composition of the two polymers films can be tailored for a variety of porosities and architectures (Bernards et al., *Soft Mater.* 2011, 6, 1621-1631; Bernards et al., *Nano Lett.* 2012, 12, 5355-5361; Lu et al., *Int. J. Pharm.* 2011, 419, 77-84; Lin et al., *J. Control. Release* 2003, 89, 179-187; Rong et al., *Int. J. Pharm.* 2012, 427, 242-251; Anzai et al., *Colloids Surfaces B Biointerfaces* 2015, 127, 292-299; Lei et al., *Eur. J. Pharm. Biopharm.* 2011, 78, 49-57; Online, V. A.; Ledeuil, J. B.; Uhart, A.; Allouche, J.; Dupin, J. C.; Martinez, H. New Insights into Micro/Nanoscale Combined. 2014, 11130-11140). Nano-porous films were created from a zinc oxide nanorod template and backed with a micro-porous support layer. Zinc oxide nanorod dimensions can be readily tuned, allowing a wide range of pores sizes and giving the ability to further refine these devices (Kim et al., *Nanotechnology* 2014, 25, 135609; Zhang et al., *Chemistry* 2005, 11, 3149-3154).

FIG. 1, Panel A schematically details the method for heat-sealing two thin-films to generate a single device. Two-step sealing decouples device shape from cell encapsulation. A first heat-sealing step controls the device size. Once the device outline is sealed, cells are inserted into the lumen of the thin-film device, and a second heat-sealing step encapsulates the cells. Device geometry can be arbitrarily selected based on the shape of the nichrome wire that defines the device seal, typically from 1 cm to 5 cm in diameter, allowing devices to be scaled to contain more cells as necessary.

Figure 2:
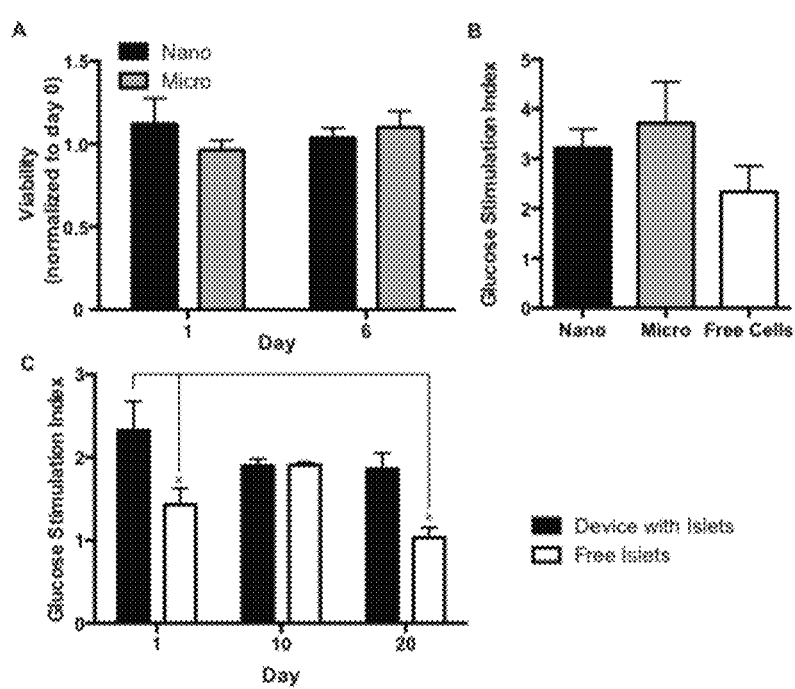
FIG. 2. In vitro device function. Panel A) In vitro device viability of encapsulated MIN6 cells as measured with mCherry fluorescence. Panel B) Glucose stimulation index of MIN6 Cells encapsulated in either micro- or nano-porous devices. Panel C) Glucose stimulation of primary islets encapsulated in micro-porous devices. ($p \leq 0.5$, $n \geq 3$)

Scanning electron microscopy (SEM) was used to visualize the micro-porous thin films, which had approximately 2 μm sized pores and a membrane thickness of approximately 10 μm (FIG. 1, panel B). Similarly, a SEM image cross-section and top-down image of a nano-porous thin-film with a micro-porous backing showed a membrane thickness of 10 μm and nano-pores ranging from 30 nm-100 nm (FIG. 1, Panel C). The thin design, flexibility, compliance of the material, and structure of the device as a whole creates a cell-encapsulating device that is easy to handle with precise membrane control (FIG. 1, Panel D). Noting that oxygen diffusion in aqueous solutions is 100 μm to 200 μm, these thin-film devices with membrane thicknesses of 10 μm decrease the proximity to vasculature needed for adequate oxygen consumption (Wendt, et al., *Adv. Mater.* 2009, 21, 3352-3367; Martin et al., *Biomaterials* 2005, 26, 7481-7503). Given the thin-film nature of the devices, the total cell content scales with device area, while the average distance of cells from the nutrient source at the device exterior is maintained, bridging the advantages of both micro- and macro-encapsulation technologies. The thin-film design of the device, coupled with rapid device vascularization will provide sufficient oxygen for encapsulated cells.

mCherry-expressing MIN6 cells encapsulated in either micro- or nano-porous devices maintain viability in vitro through 6 days, as defined by the persistence in mCherry signal, and are able to maintain glucose stimulated insulin secretion (FIG. 2, Panel A). The glucose stimulation index is a metric to quantify beta cell function by comparing the ratio of insulin release in a high glucose state relative to a resting state. MIN6 cells encapsulated in either micro- or nano-devices demonstrate no statistically significant changes in their glucose stimulation index (FIG. 2, Panel B). Furthermore, freshly isolated mouse islets encapsulated in these devices maintain their glucose stimulation index over a period of 20 days in vitro, which is significantly improved over free islets alone, which have over a 25% decrease in the glucose stimulation index from day 1 (FIG. 2, Panel C). This demonstrates that beta cell insulin response to glucose is maintained within both nano- and micro-porous thin-film devices. Furthermore, glucose sensing and insulin secretion, a major function of beta cells, is unaffected by encapsulation in either micro- or nano-devices.

Figure 3:
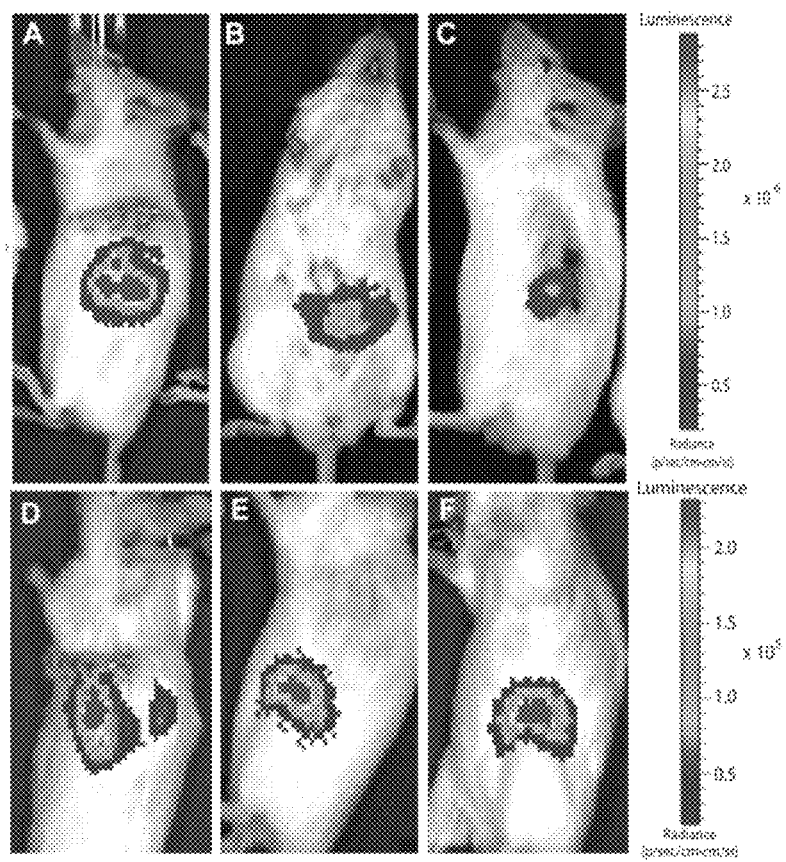
FIG. 3. In vivo device image and tracking. Panel A) Device with encapsulated MIN6 cells implanted in the subcutaneous space of the mouse dorsal. Panel B) Device with encapsulated MIN6 cells implanted under the mouse skin and muscle over the liver. Panel C) No device control with cells implanted directly into the kidney capsule. Panel D) Device with encapsulated MIN6 cells implanted after 1 day, Panel E) 30 days, Panel F) 90 days.

Viability and persistence of transplanted cells can be monitored in recipient mice in real time using bioluminescence imaging. This technique was used to monitor in vivo luciferase-expressing MIN6 (MIN6.LUC) cells encapsulated into thin-film devices implanted under the abdomen above the liver (FIG. 3, Panel A) or over the muscle layer in the subcutaneous space of the mouse dorsal flank (FIG. 3, Panel B) or unencapsulated cells implanted into the kidney capsule (FIG. 3C) of syngeneic B6 mice. The thin-film device design is compatible with bioluminescence imaging and thus allows tracking of encapsulated cells in vivo. Luciferase-expressing MIN6.LUC cells were encapsulated into thin-film devices and the devices were implanted under the abdomen above the liver or over the muscle layer in the subcutaneous space of the mouse dorsal flank (FIG. 3, Panels D-F). Bioluminescent signal decreases with device implant depth, and both implanted device locations were visually brighter than the no device kidney capsule control. Persistence of bioluminescent signal demonstrates maintained viability through 90 days of implantation. As the bioluminescent signal tracks with device location, it also provides a non-invasive method to track device movement. Because the encapsulated cells are not fixed within the device, and the device itself is not sutured or tethered to any tissue, cellular reorganization of the encapsulated cells or daily movement of the mouse can result in the movement of the bioluminescent signal.

Figure 4:
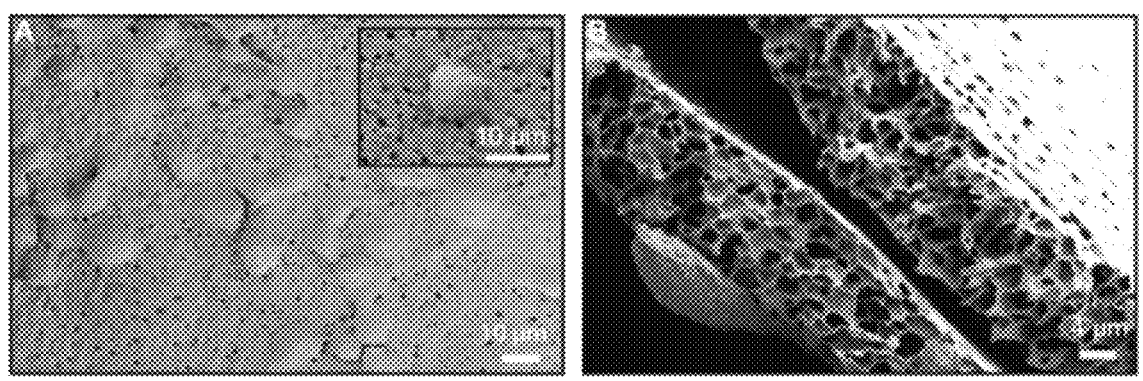
FIG. 4. Micro-porous barrier inhibits cell invasion. Panel A) Top down SEM image of cells attached to the exterior surface of the micro-porous thin-film device after 1 month in vivo. Panel B) Cross-section SEM image of the micro-porous thin-film device after 1 month in vivo, demonstrating membrane integrity and isolation of internal and external cells.
Figure 5:
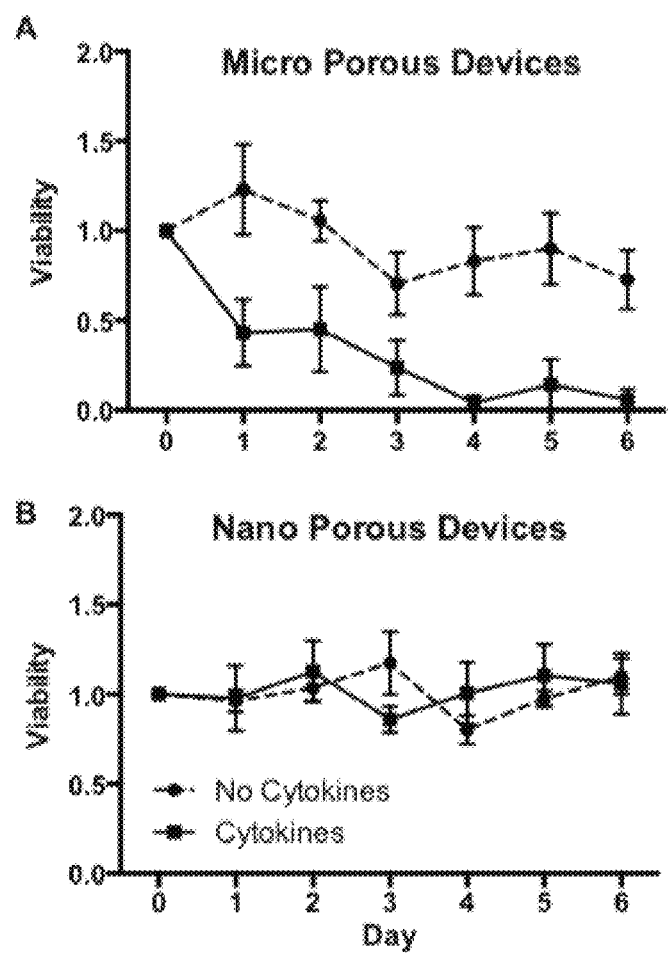
FIG. 5. Cytokine protection. Viability of cells within a micro-porous device (Panel A) and a nano-porous device (Panel B) over 1 week, with (solid line) and without (dashed lines) cytokines. ($n \geq 4$)
Figure 7:
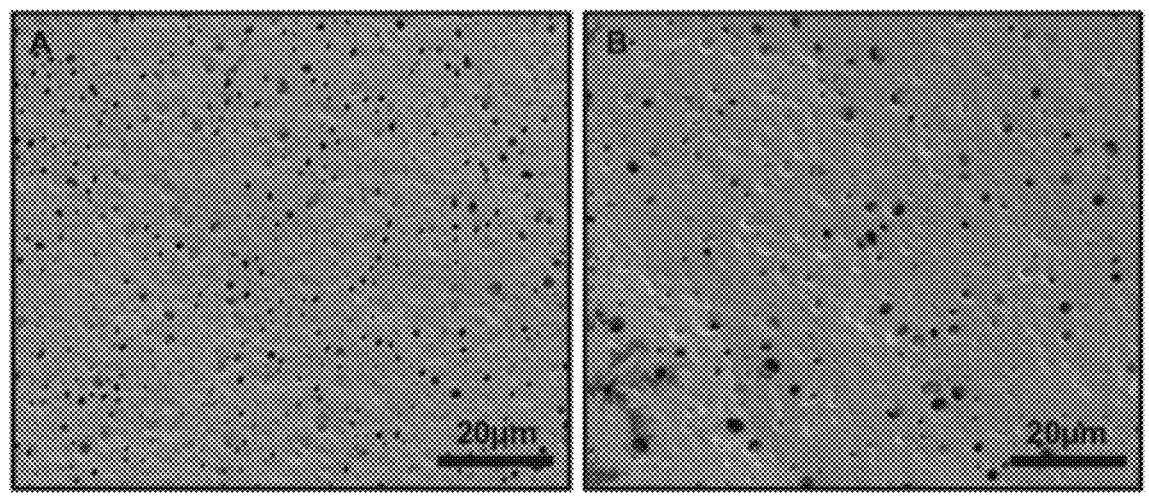
FIG. 7. Device exterior SEM. Panel A) Device exterior prior to implantation. Panel B) Device exterior after 2 months in vivo.
Figure 8:
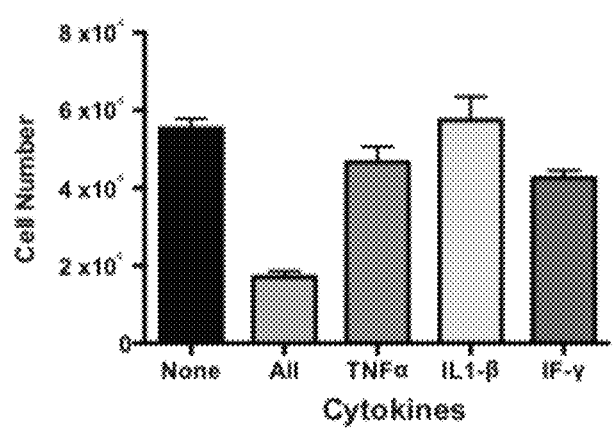
FIG. 8. Cytokines affect cell viability. Cell number was quantified by a cyquant assay (−) no cytokine control, (+) a combination of cytokines with TNF alpha, IL1 beta and IF gamma, and TNF alpha, IL1 beta and IF gamma individually.

Ideal immune protection requires physically excluding immune cells as well as restricting diffusion of immune mediators such as cytokines that are toxic to beta cells. By encapsulating cells in micro-porous devices, cell-contact-mediated immune protection may be achieved, and additional cytokine-mediated immune protection may be accomplished with the nano-porous devices. Cells encapsulated in thin-film devices are physically compartmentalized from the in vivo environment, as clearly seen in FIG. 4, Panel A, where cells are attached to the outer surface of the device but no infiltration into the device lumen was found. Despite cell adhesion on device surfaces, pores remain unclogged (FIG. 7) most likely due to the limited fibrotic response of the surrounding tissue. FIG. 4, Panel B shows a SEM cross-section, with a cell attached to the external surface of a device. No cellular processes are seen extending into the device, further confirming the ability of the device to prevent cell-contact-mediated interaction by isolating the encapsulated cells from the surrounding in vivo tissue. By further controlling the porosity of the membrane, cytokine-mediated immune protection may additionally be achieved. Tumor necrosis factor $\alpha$ (TNF$\alpha$), interleukin 1 $\beta$ (IL1$\beta$), and interferon $\gamma$ (IFN$\gamma$) inflammatory cytokines are known to kill beta cells individually, and act synergistically when present in combination. They were chosen in order to test the devices' ability to protect from cytotoxic cytokines (Tracey, K. J. The Inflammatory Reflex. 2002, 420, 853-859; Bastiaens, P. When It Is Time to Die. 2009, 459; Libert, C. A Nervous Connection. 2003, 421, 328-329; Wang et al., *Cell* 2008, 133, 693-703.). (FIG. 8) (Fonseca et al., *Int. Immunopharmacol.* 2014; Roff et al., *Front. Immunol.* 2014, 4, 498; Yang et al., *Mol. Endocrinol.* 2014, me20131257). Interestingly, whereas micro-porous thin-film devices failed to maintain cell viability (FIG. 5, Panel A), the use of a nano-porous layer in these thin-film devices mitigated the cytokine-mediated decrease in viability (FIG. 5, Panel B). It is unclear if cytokines are completely isolated from the lumen of devices, given the size of cytokines in relation to the nano-pores, a portion of cytokines are expected to pass through the membrane. The protection by nano-porous devices would result from limited transport and diffusion of cytokines though the membrane, such that the cells are unresponsive to the reduced cytokine concentrations. Considering that the cytokine cocktail concentration used exceeds known cytotoxic concentrations by 10-fold, we expect that the majority of the cytokines to be limited by the nano-porous barrier. This further highlights how micro-porous and nano-porous membranes can be used to control desired cell responses.

Figure 6:
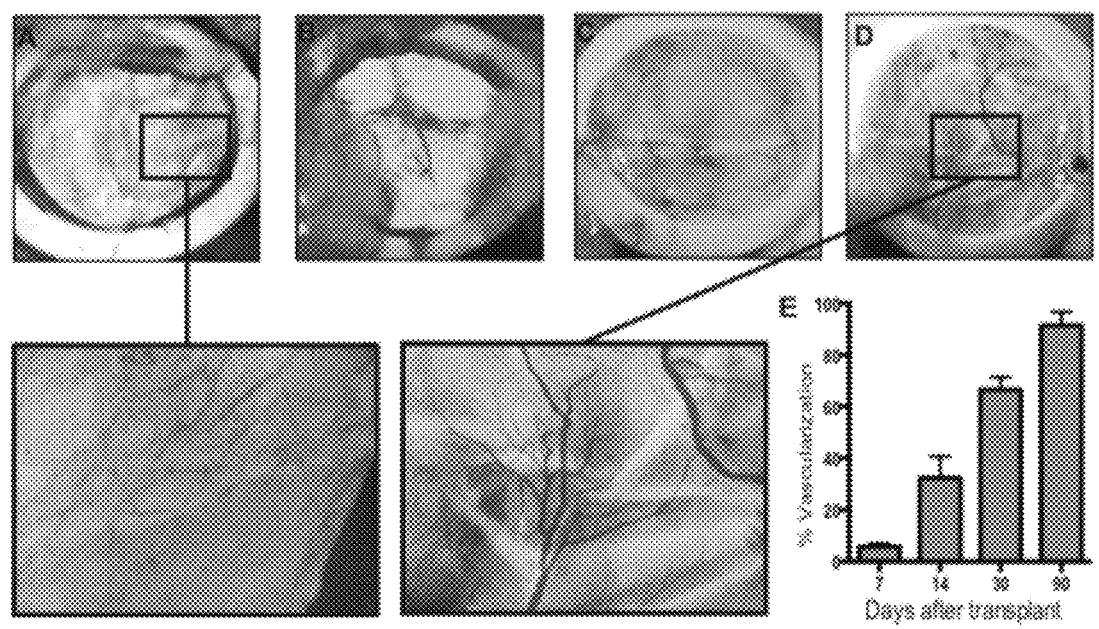
FIG. 6. Device vascularization. Bright field images of devices implanted after Panel A) 7 days, Panel B) 14 days, Panel C) 30 days and Panel D) 90 days, with magnified images at day 7 and day 90. Panel E) Quantification of device vascularization from day 7 to day 90. (n=3)
Figure 9:
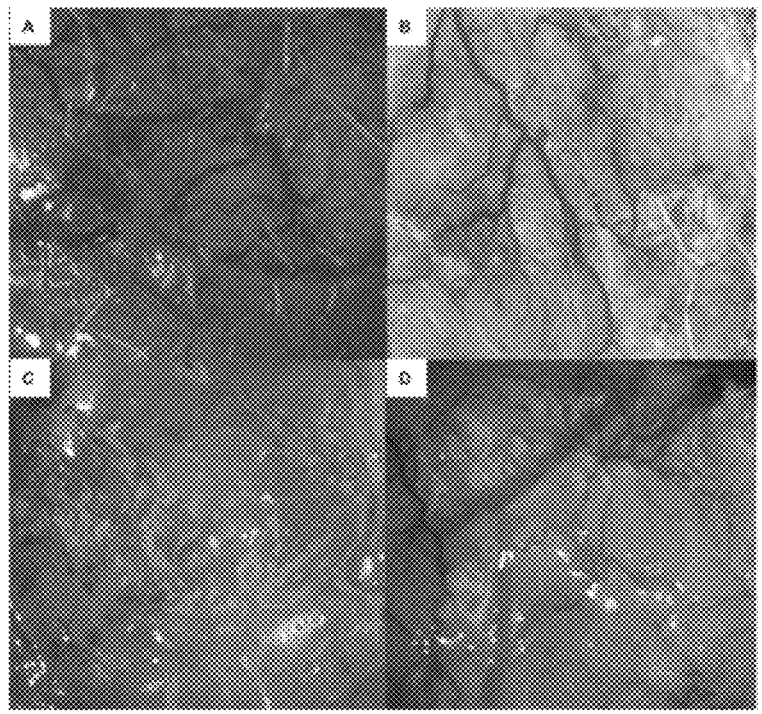
FIG. 9. Cell-free devices controls for device vascularization. Bright field images of devices implanted after 50 days Panel A) Porous-PCL, Panel B) Non-porous PCL, Panel C) PLGA, and Panel D) PVDF.
Figure 10:
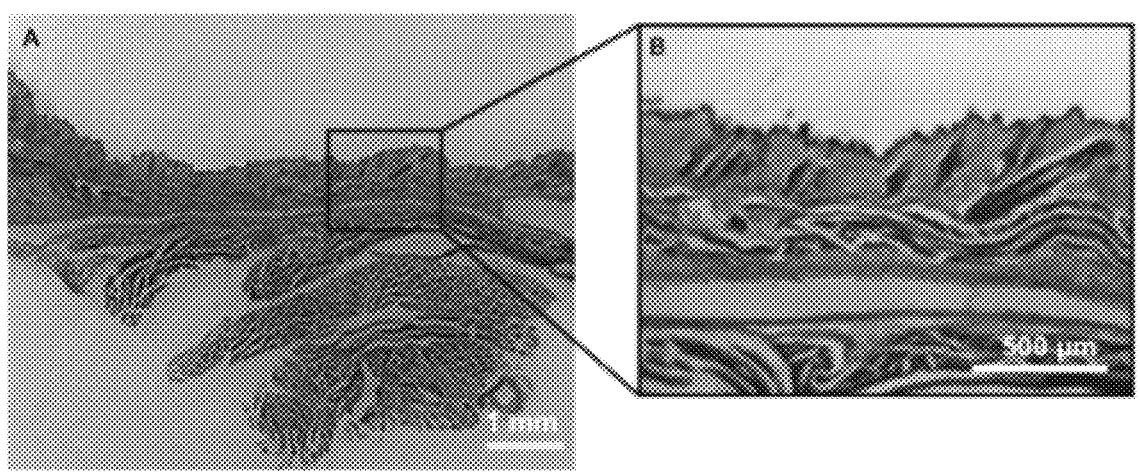
FIG. 10. Histology of devices. Panel A) Cross section of a device after 2 months in vivo, with Masson trichrome staining. Panel B) Magnification of device cross-section, demonstrating minimal fibrotic response.

Device vascularization in vivo is imperative for long-term survival of encapsulated cells. Vascularization surrounding cells encapsulated in thin-film devices is important for function and survival of encapsulated cells. To monitor the state of device vascularization, devices were implanted, then removed and imaged at 7, 14, 30 and 90 days (FIG. 6, Panels A-D). The first visible signs of vascularization of cell encapsulated thin-film devices were observed 14 days after implantation (FIG. 6, Panel B). These devices demonstrate a steady increase in vivo vascularization of 1.5% daily over a 2-month period (FIG. 6, Panel E). Vascularization of these PCL devices occurred without any supplementary additional proangiogenic factors, as shown with implanted cell-free devices with similar vascularization (FIG. 9, Panels A,B). When compared with common polymeric implant materials PLGA (FIG. 9, Panel C) and PVDF (FIG. 9, Panel D), PCL cell-free devices exhibited noticeably more developed and branched vasculature. Furthermore, a relatively minimal foreign body response was observed (FIG. 10).

Figure 11:
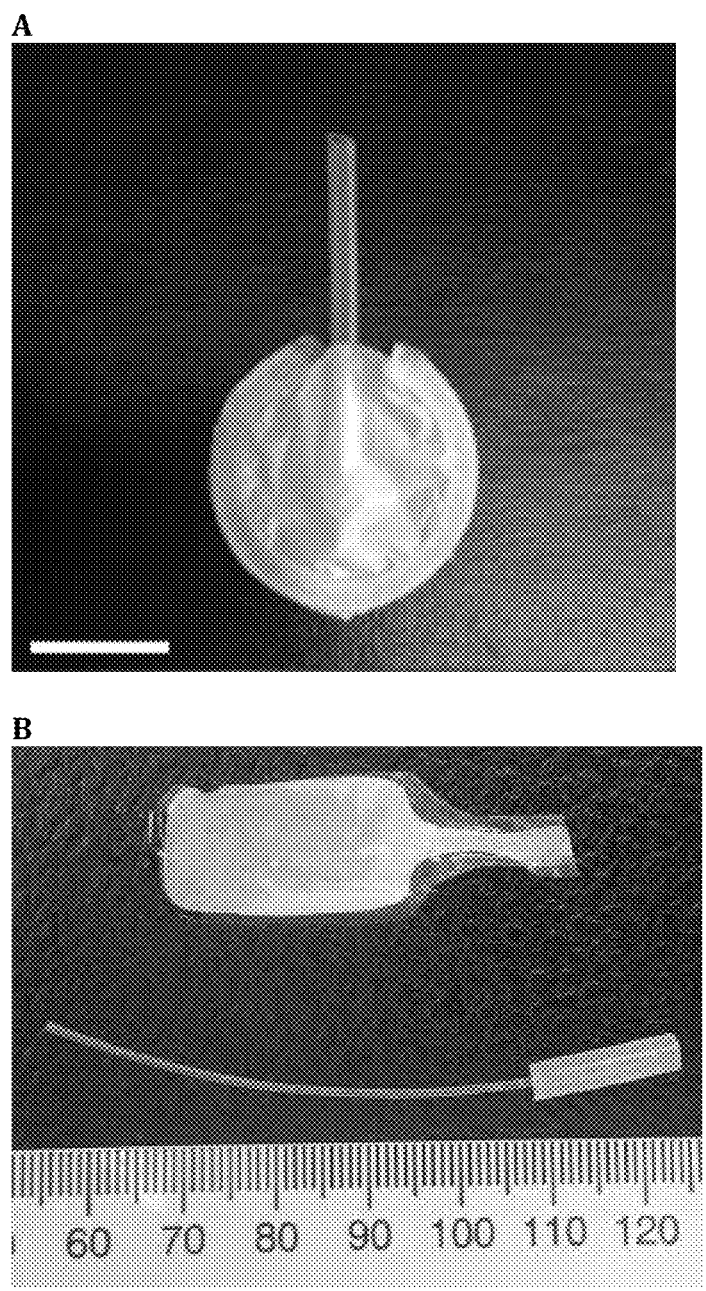
FIG. 11. Exemplary thin film devices. Panel A) A circular thin film device including an opening for access to the device lumen, the opening includes a tube for accessing device lumen. Panel B) A rectangular device with a thin elongated opening and a tube for accessing device lumen.

FIG. 11, Panel A depicts a PCL thin film device. The device includes two nanoporous layers in between which a lumen is defined. Each of the nanoporous layers have a microporous backing for structural support. The two nanoporous layers are attached to each other at the periphery of the device all along the circumference, other than an inlet region at which the layers are not in contact with each other and define an opening into the lumen of the device. A plastic tubing is inserted into the opening and held in place between the two layers. In addition, a third layer of 1 mm-2 mm thick PCL layer is disposed along the periphery of the device to increase the rigidity at the periphery. FIG. 11, Panel B depicts another embodiment of a PCL thin film device having two nanoporous layers (each having a microporous backing) in between which a lumen is defined.

Figure 12:
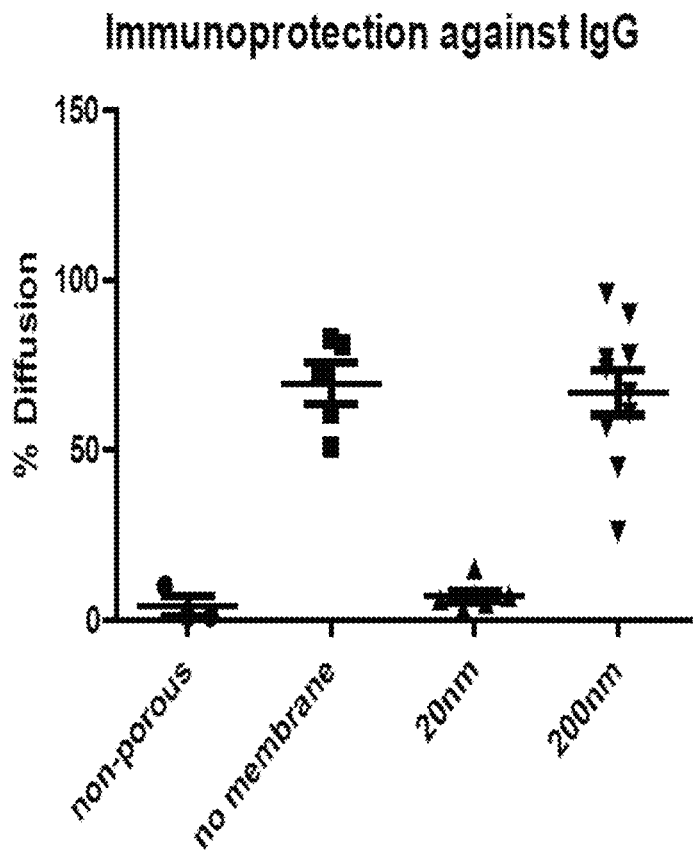
FIG. 12. Graph demonstrating that 20 nm PCL membranes limit diffusion of IgG.

FIG. 12 depicts the result of diffusion of IgG across a non-porous layer, a 20 nm porous layer and a 200 nm porous layer. Three different thin layer PCL devices were constructed. Each of the devices includes two PCL layers attached to each other at the periphery of the device all along the circumference, other than an inlet region at which the layers are not in contact with each other and define an opening into the lumen of the device. A non-porous membrane device was constructed using two PCL layers into which nanopores or micropores were not introduced during manufacturing. A 20 nm porous membrane device was constructed using two nanoporous layers each having an average pore diameter of 20 nm and structurally supported by a microporous backing layer. A 200 nm porous membrane device was constructed using two microporous layers each having an average pore size of 2 µm and a connectivity diameter of 200 nm. IgG was loaded into each device and then the device was sealed shut, the device was then allowed to soak in a standard buffered saline solution where the release of IgG from the device lumen to the external solution through the porous layers was measured using a standard protein measurement assay.

Figure 13:
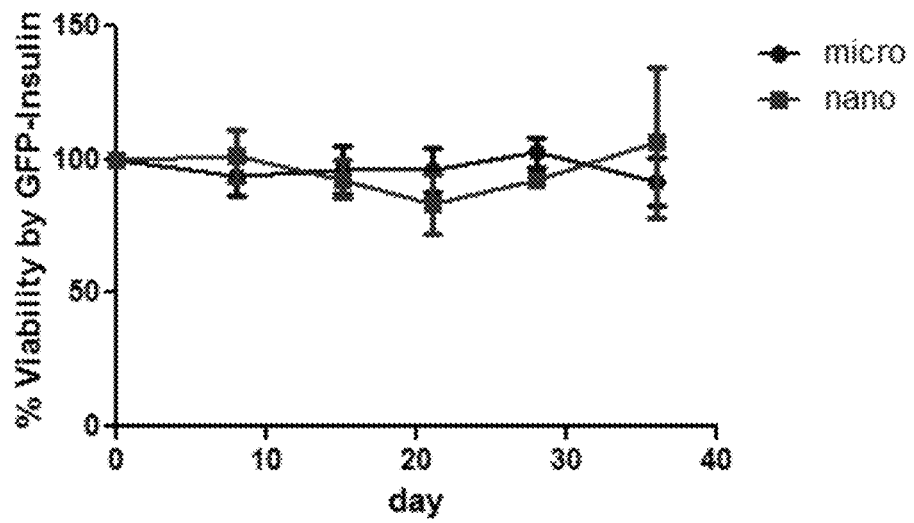
FIG. 13. Graph demonstrating that human embryonic stem (hES) green fluorescent (GFP)-insulin cells encapsulated in nano- or macro-porous devices are viable for up to 5 weeks in vitro.

FIG. 13 illustrates that hES GFP-Insulin cells are viable for 40 days in either a microporous or nanoporous thin film device prepared according to the methods disclosed herein. The microporous device used to generate the data was made from two microporous PCL layers having ~2 µm wide pores formed in a ~10 µm thick PCL film (the through channels in the film has a connectivity diameter of about 200 nm). The nanoporous device used to generate the data was made from two nanoporous PCL layers having 30 nm-100 nm wide pores formed in a ~10 µm thick PCL film. The device was subcutaneously implanted into the dorsal flank of BalbC mice.

Figure 14:
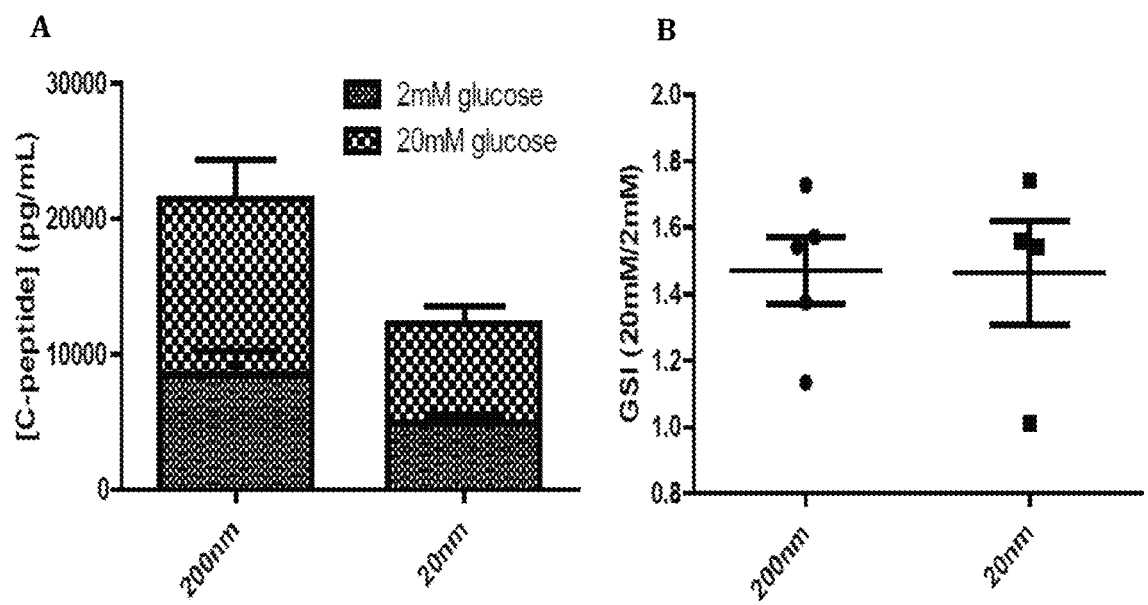
FIG. 14. Panel A depicts release of c-peptide from islet cells encapsulated in a device having a polymer layer with about 2 μm diameter pore (200 nm connectivity) or with about 20 nm pore size. Panel B depicts glucose stimulation index (GSI) of encapsulated islet cells.

FIG. 14 the same devices as used for FIG. 12 were utilized. Panel A depicts c-peptide release from islet cells encapsulated in a 200 nm porous membrane device or a 20 nm porous membrane device. The islet cells in the device were exposed to a medium containing 2 mM glucose or 20 mM glucose solution. The culture supernatant was collected at 30 min after exposure to the 2 mM or 20 mM glucose. Insulin protein content in the culture supernatant was measured using an enzyme linked immunosorbent assay (Mercodia). Panel B illustrates glucose stimulation index (calculated as the ratio of insulin secreted at high-to-low glucose conditions).

Figure 15:
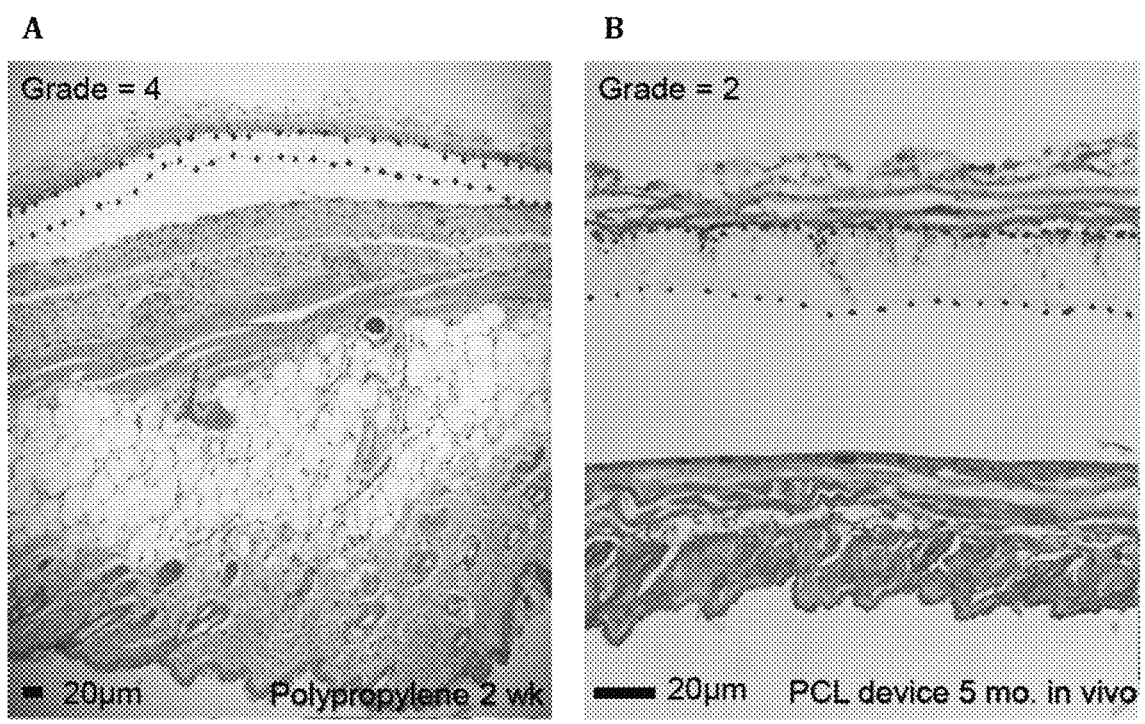
FIG. 15. Panel A) Polypropylene thin film device shows a significant foreign body response (FBR) within 2 weeks after transplantation. Panel B) A PCL thin film device induces minimal FBR 5 months after transplant.

FIG. 15 shows foreign body response (FBR) to a thin film device made from polypropylene (Panel A; Grade 4) and from a PCL device made according to the methods disclosed herein (Panel B; Grade 2). The polypropylene (PP) thin film device includes two thin layers of PP cut to the same size as the PCL device. The PP layers were non-porous. The PCL device included two PCL layers, where one layer was microporous and the other layer was nanoporous. The PP device was transplanted subcutaneously into the dorsal flank of a BalbC mouse and assayed after 2 weeks. The PCL device was transplanted subcutaneously into the dorsal flank of a BalbC mouse and assayed after 5 months.

Figure 16:
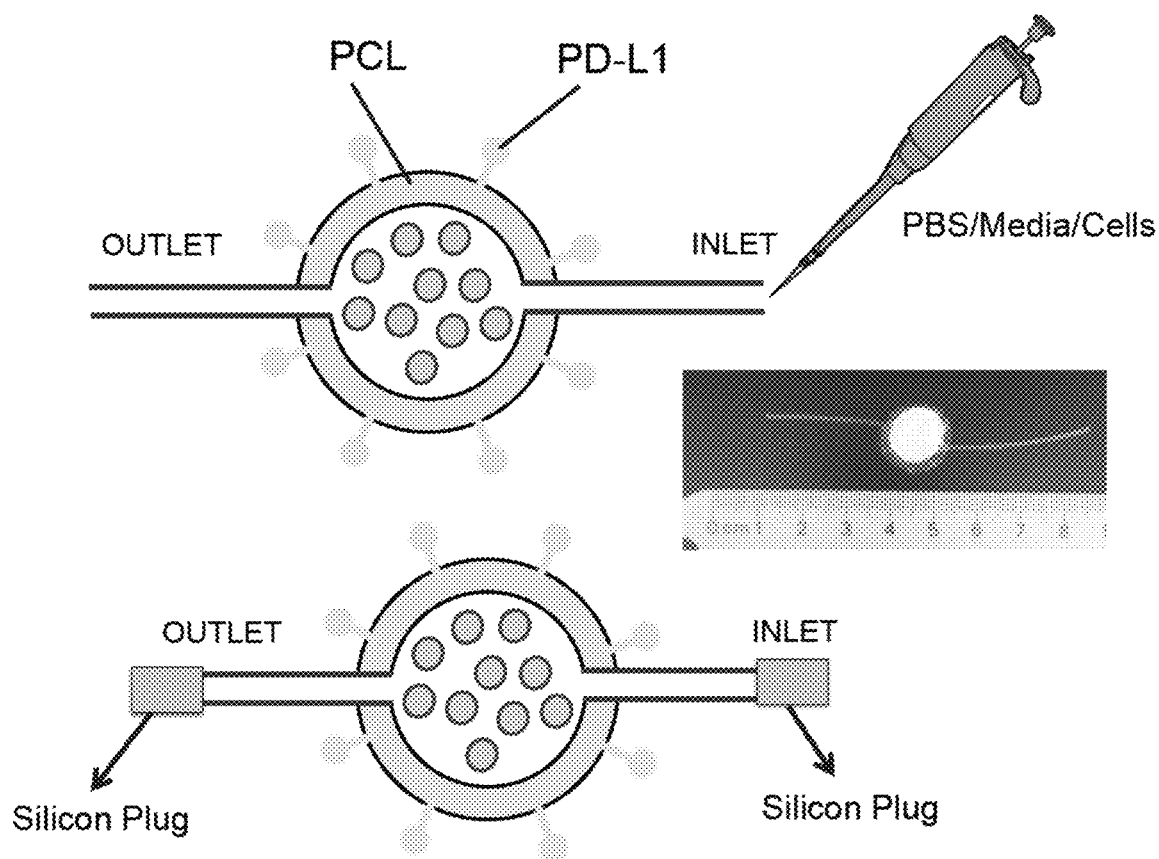
FIG. 16. Exemplary thin film devices showing means for inlet to and outlet from the devices.

FIG. 16 depicts a schematic of a thin film device having two openings into the lumen formed between the thin film layers. The two openings hold in place an inlet tube and an outlet tube. The inlet and outlet tubes may be closed between use by using plugs, such as silicon plugs. The thin film device may also include a molecule (e.g., PD-L1 protein) to suppress the immune system.

The inventors have demonstrated the successful fabrication and use of an innovative cell-encapsulating device that combines the some of the benefits of both micro- and macro-encapsulation strategies. A flexible thin-film geometry allows precise membrane porosity selection to direct desired cellular responses and interactions while maintaining a normal glucose response of encapsulated beta cells. A small reservoir volume allows a rapid response to external stimuli, limiting dilutional interference from the device reservoir. Similar to micro-encapsulation devices with large surface area to volume ratios, the thin-film device structure described herein is uninhibited by device thickness. Moreover, cells encapsulated in either micro- or nano-devices demonstrate a glucose stimulation index consistent with unencapsulated cells, indicating glucose sensing and responsive insulin secretion is successfully preserved. The devices described herein allow sufficient bioluminescence transmission through the device membrane to be measured with in vivo imaging systems. As demonstrated in vivo, the device membranes create a physical barrier between encapsulated cells and the host environment, physically preventing cell contact initiated signaling. Furthermore, incorporation of a nano-porous membrane enables these devices to obstruct cytokine passage and protect encapsulated cells from cytokine-mediated cell death. Additionally, in vivo studies show vascularization around the devices with limited fibrosis, suggesting great promise for this device as a long-term cell encapsulation device.

The thin film cell encapsulation devices for cell transplantation described herein can be used to directly investigate the cell contact-dependent or soluble factor-mediated signaling by controlling pore dimensions-inhibiting specific interactions. These devices have the capacity to prevent immune cell contact with encapsulated cells, and the nanoporous device can protect encapsulated cells from cytokine-induced cell death. Additional uses include using these devices in vivo to investigate modes of immune attack, whether contact- or soluble factor-mediated. These thin-film PCL devices have great potential as implantable cell-encapsulation devices for treating diseases, such as Type 1 Diabetes.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a subject in need of a therapeutic molecule, said method comprising:
   (a) introducing into said subject a device comprising:
      (i) a lumen containing a plurality of cells capable of secreting the therapeutic molecule; and
      (ii) a layer comprising a biocompatible polymer surrounding said lumen and comprising a plurality of pores sized such that said therapeutic molecule can diffuse from said device, wherein said plurality of pores are nanopores; and
   (b) secreting, from said plurality of cells, said therapeutic molecule at a therapeutically effective amount for at least 30 days, wherein said plurality of cells are selected from the group consisting of: allogeneic cells and xenogeneic cells, and wherein said subject has not received immunosuppression therapy.

2. The method of claim 1, wherein said layer of biocompatible polymer comprises a first layer of biocompatible polymer and a second layer of biocompatible polymer, wherein said lumen is disposed between said first layer of biocompatible polymer and said second layer of biocompatible polymer.

3. The method of claim 1, wherein said biocompatible polymer is selected from the group consisting of: methacrylate polymer, polyethyleneimine, polyethyleneimine-dextran sulfate, poly(vinylsiloxane) ecopolymerepolyethyleneimine, phosphorylcholine, poly(ethyl methacrylate), polyurethane, poly(ethylene glycol), poly(lactic-glycolic acid), hydroxyapatite, poly(lactic acid), polyhydroxyvalerte and copolymers thereof, polyhydroxybutyrate and copolymers thereof, polycaprolactone, polydiaxanone, polyanhydride, polycyanocrylate, poly(amino acids), poly(orthoesters), polyesters, collagen, gelatin, cellulose polymer, chitosans, alginates, and any combination thereof.

4. The method of claim 3, wherein said biocompatible polymer comprises polycaprolactone.

5. The method of claim 1, wherein said therapeutic molecule has a molecular weight of less than 10 kDa.

6. The method of claim 1, wherein said therapeutic molecule has a hydrodynamic radius of less than 2 nm.

7. The method of claim 1, wherein said plurality of pores are sized such that a concentration of cytokines that is capable of accessing said lumen is below a level required for an immune response against said plurality of cells.

8. The method of claim 7, wherein said cytokines have a molecular weight of greater than 15 kDa.

9. The method of claim 7, wherein said cytokines have a hydrodynamic radius of greater than 2 nm.

10. The method of claim 7, wherein said cytokines are selected from the group consisting of: interferons, interleukins, and tumor necrosis factors.

11. The method of claim 1, wherein said nanopores have an average diameter from 5 nm to 500 nm.

12. The method of claim 1, wherein said nanopores have an average diameter from 10 nm to about 300 nm.

13. The method of claim 1, wherein said first layer of biocompatible polymer and said second layer of biocompatible polymer each have a thickness of less than 15 µm.

14. The method of claim 1, wherein said device has a thickness of less than 30 µm.

15. The method of claim 1, wherein said introducing comprises transplanting said device subcutaneously into said subject.

16. The method of claim 1, wherein said subject has or is predisposed to developing Type I diabetes.

17. The method of claim 16, wherein said plurality of cells comprise insulin-secreting cells.

18. The method of claim 17, wherein said therapeutic molecule is insulin.

19. The method of claim 17, wherein said insulin-secreting cells have a glucose stimulation index (GSI) that is not statistically significantly changed over a period of at least 30 days after introducing said device into said subject.

20. The method of claim 1, wherein said device is substantially planar.

* * * * *